US012766159B2

(12) United States Patent
Lee et al.

(10) Patent No.: US 12,766,159 B2
(45) Date of Patent: Oct. 20, 2026

(54) GLYCYRRHIZIN-BRANCHED POLYETHYLENE GLYCOL CONJUGATE FOR TREATING CANCER

(71) Applicant: IUCF-HYU (INDUSTRY-UNIVERSITY COOPERATION FOUNDATION HANYANG UNIVERSITY), Seoul (KR)

(72) Inventors: Dong Yun Lee, Seoul (KR); Min Su Kim, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 294 days.

(21) Appl. No.: 18/695,221

(22) PCT Filed: Sep. 28, 2022

(86) PCT No.: PCT/KR2022/014578
§ 371 (c)(1),
(2) Date: Mar. 25, 2024

(87) PCT Pub. No.: WO2023/055081
PCT Pub. Date: Apr. 6, 2023

(65) Prior Publication Data

US 2024/0398843 A1 Dec. 5, 2024

(30) Foreign Application Priority Data

Sep. 28, 2021 (KR) ........................ 10-2021-0128218

(51) Int. Cl.
*A61K 31/704* (2006.01)
*A61K 47/60* (2017.01)
*A61P 35/00* (2006.01)

(52) U.S. Cl.
CPC ............ *A61K 31/704* (2013.01); *A61K 47/60* (2017.08); *A61P 35/00* (2018.01)

(58) Field of Classification Search
CPC ................................ A61K 31/04; A61K 47/60
See application file for complete search history.

(56) References Cited

U.S. PATENT DOCUMENTS

2018/0036418 A1 2/2018 Yu et al.

FOREIGN PATENT DOCUMENTS

| | | |
|---|---|---|
| KR | 10-2008-0044639 A | 5/2008 |
| KR | 10-2009-0089316 A | 8/2009 |
| KR | 10-2009-0118879 A | 11/2009 |
| KR | 10-2019-0036482 A | 4/2019 |

OTHER PUBLICATIONS

Rossum, Clinical Therapeutics/vol. 21, No. 12, 1999. (Year: 1999).*
Swierczewska, Expert Opin Emerg Drugs, 2015; 20(4): 531-536. (Year: 2015).*
International Search Report issued from the WIPO dated Jan. 17, 2023 for the PCT International Application No. PCT/KR2022/014578.
Written Opinion of International Search Authority issued from the WIPO dated Jan. 17, 2023 for the PCT International Application No. PCT/KR2022/014578.

* cited by examiner

*Primary Examiner* — Layla D Berry

(57) ABSTRACT

The present invention relates to a glycyrrhizin-branched polyethylene glycol conjugate and a use thereof for treating cancer, wherein the glycyrrhizin-branched PEG conjugate exhibits anti-cancer effects better than those of glycyrrhizin and increases blood half-life, and thus can be effectively used for treating cancer.

7 Claims, 30 Drawing Sheets

10.5PEGGL 100; Date Acquired: 6/21/2021 4:19:04 PM KST; Vial: 57; Inj. #: 1; Channel: ****

Sample Name: 10.5PEGGL 100
Vial: 57
Inj. #: 1
Date Acquired: 6/21/2021 4:19:04 PM KST Processed Channel: W2489 Ch.A 254nm

| | Peak Name | Processed Channel | Retention Time (min) | Area | %Area | Height | Amount | Units |
|---|---|---|---|---|---|---|---|---|
| 1 | GL | W2489 Ch.A 254nm | 2.154 | 152565 | 68.23 | 27109 | 27.1 | ug/ml |

DW 80%DW 60% DW 40% DW 20% DW PBS

Control DW % per PBS 420nm UV abs

| Group | DW | 80%DW | 60%DW | 40%DW | 20%DW | PBS |
|---|---|---|---|---|---|---|
| 420nm UV abs | 2.230 ±0.05 | 2.185 ±0.04 | 1.965 ±0.02 | 0.085 ±0.006 | 0.032 ±0.004 | 0.028 ±0.004 |

PBS DW 1mg/ml 0.8mg/ml 0.6mg/ml 0.4mg/ml 0.2mg/ml

GL

420 UV abs

| Group | DW | PBS | GL 1mg/mL | bPEG-GL 1mg/mL |
|---|---|---|---|---|
| 420nm UV abs | 2.230 ±0.05 | 0.028 ±0.004 | 0.035 ±0.005 | 0.026 ±0.005 |

PBS DW 3.6mg/ml 2.88mg/ml 2.16mg/ml 1.44mg/ml 0.72mg/ml bPEG-GL (GL equi)

GLYCYRRHIZIN-BRANCHED POLYETHYLENE GLYCOL CONJUGATE FOR TREATING CANCER

CROSS-REFERENCE TO RELATED APPLICATIONS

This application is a National Stage Entry of PCT International Application No. PCT/KR2022/014578, which was filed on Sep. 28, 2022, and which claims priority from and the benefit of Korean Patent Application 10-2021-0128218, filed with the Korean Intellectual Property Office on Sep. 28, 2021. The disclosure of the above patent application is hereby incorporated by reference in its entirety.

TECHNICAL FIELD

The present invention relates to a glycyrrhizin-branched polyethylene glycol conjugate and its use for treating cancer.

BACKGROUND ART

Globally, cancer incidence and mortality are increasing every year. There are various types of cancer therapeutic agents, ranging from traditionally used cytotoxic anticancer agents to recently developed targeted anticancer agents. Existing cytotoxic anticancer agents affect not only cancer cells but also normal cells, exhibiting systemic toxicity and cytotoxicity, resulting in various side effects. To overcome the limitations of cytotoxic anticancer agents, research and development on monoclonal antibody treatments that target and kill only cancer cells is being continuously conducted. The monoclonal antibodies approved by the US Food and Drug Administration (FDA) include cetuximab, avelumab, rituximab, and ipilimumab. However, recent clinical results show that the efficacy of some monoclonal antibodies is significantly reduced in patients with genetic mutations located downstream of receptors in the intracellular signaling system.

Hepatocellular carcinoma (HCC) is the most representative type of liver cancer. HCC is a dangerous disease that ranks third in cancer mortality and ranks sixth in cancer incidence worldwide. Treatment through surgery is known to be the most representative method, but surgery not only has a high relapse rate but also the potential risk of metastasis to other organs. Therefore, research is being actively conducted to treat HCC with a drug rather than surgery.

DETAILED DESCRIPTION OF DISCLOSURE

Technical Problem

In the above situation, the inventors studied a method for maximizing the anticancer effect of glycyrrhizin and confirmed that conjugating branched polyethylene glycol to glycyrrhizin increases the effect of inducing apoptosis and cell cycle arrest of cancer cells, compared to glycyrrhizin alone, and also increases the half-life of glycyrrhizin in blood.

Therefore, the present invention is directed to providing a glycyrrhizin-branched polyethylene glycol conjugate and a use thereof for treating cancer.

Technical Solution

Glycyrrhizin is a natural substance extracted from the roots of licorice, and an amphipathic molecule consisting of hydrophilic glucuronic acid and hydrophobic glycyrrhetinic acid. Glycyrrhizin is known to be a major inhibitor of high mobility group box 1 (HMGB-1) that promotes extracellular cancer growth and metastasis, and also has anti-inflammatory and antiviral effects. Glycyrrhizin is known to have an anticancer effect through various mechanisms in addition to its inhibitory effect on HMGB-1, and typically, it inhibits cancer growth by suppressing the action of various proteins including cyclin D1 that induces cancer cell growth by blocking the Akt/mTOR pathway (Int J Clin Exp Pathol. 2015; 8 (5): 5175-5181. Glycyrrhizic acid inhibits leukemia cell growth and migration via blocking AKT/mTOR/STAT3 signaling; Front. Oncol., 12 Apr. 2013. Role of PI3K-AKT-mTOR and Wnt signaling pathways in transition of G1-S phase of cell cycle in cancer cells). However, glycyrrhizin is known to bind to proteins in blood, so the half-life of glycyrrhizin is reduced when injected intravenously. Additionally, there is a problem that, when blood proteins and glycyrrhizin are combined, the anticancer effect may also be reduced.

Therefore, the inventors invented a method of PEGylating glycyrrhizin to maximize an anticancer effect by increasing the half-life of glycyrrhizin.

The term "PEGylation" used herein refers to conjugating polyethylene glycol (PEG) to a material. PEG is a biocompatible polymer approved by the FDA and is currently used to improve hydrophilicity in various drugs.

Specifically, first, glycyrrhizin is oxidized to form a carbonyl group and then allowed to react with various types of branched PEG. Since PEGylation technology is already known in the art to which the present invention belongs, it can be seen that the PEGylation of glycyrrhizin is easy. However, as a result of the experiment, glycyrrhizin binds only to specific branched PEG (Comparative Example).

Accordingly, one aspect of the present invention provides a conjugate that includes (a) glycyrrhizin; and (b) branched polyethylene glycol covalently linked to the glycyrrhizin, wherein the branched polyethylene glycol is 4-arm polyethylene glycol and has a molecular weight of 1 to 4 kDa.

The term "branched PEG" is one in which polymerizable PEG (H—(O—$CH_2$—$CH_2$)n-OH) is polymerized to the parent nucleus ($CH_4$) in a branched form, and its molecular weight is determined by n.

The branched PEG of the present invention has four branches, and its molecular weight may be 1 to 4 kDa, or 1 to 3 kDa, and preferably, 2 kDa.

In one embodiment of the present invention, the glycyrrhizin may be modified without losing its original properties into, for example, an oxidized form. Specifically, as shown in FIG. 2, in the oxidized glycyrrhizin, a carbonyl group may be formed by opening the bond between the C2 and C3 of the terminal glucuronic acid ring by oxidation.

In one embodiment of the present invention, the branched PEG and glycyrrhizin are linked by a covalent bond, and the covalent bond may be an amide bond, a carbonyl bond, an ester bond, a thioester bond, or a sulfonamide bond.

More preferably, the covalent bond may be an amide bond formed by reacting a carbonyl group of glycyrrhizin oxidized by treatment with sodium periodate and an amine group of branched PEG. Accordingly, the branched PEG may be PEG-amine.

In one embodiment of the present invention, when covalently bonded, the binding molar ratio between glycyrrhizin and the branched PEG, that is, the binding ratio between the branched PEG and glycyrrhizin molecules may be 1:0.5 to 1:5, more preferably, 1:0.5 to 1:3, and most preferably, 1:1, but the present invention is not limited thereto.

In one embodiment of the present invention, glycyrrhizin has an increased anticancer effect through PEGylation: the inhibition of angiogenesis (FIG. 7), increased endocytosis (absorption) (FIG. 9), an increased inhibitory effect on cancer cell migration (FIG. 10), increased effects of inducing apoptosis and cell cycle arrest of cancer cells (FIGS. 11 and 12), and an improved effect of retention in the body (FIG. 13).

In one embodiment of the present invention, the blood half-life of glycyrrhizin was increased through PEGylation (FIG. 14). Accordingly, the conjugate may be administered orally and parenterally, and is preferably administered parenterally, for example, by intravenous injection.

Accordingly, another aspect of the present invention provides a pharmaceutical composition for preventing or treating cancer, which includes the conjugate as an active ingredient.

In the pharmaceutical composition for preventing or treating cancer, since the content related to the conjugate is the same as described above, the description of overlapping content will be omitted.

In the present invention, the cancer may be selected from the group consisting of liver cancer, brain tumor, breast cancer, lung cancer, ovarian cancer, colon cancer, pancreatic cancer, cervical cancer, kidney cancer, stomach cancer, prostate cancer, uterine cancer, and bladder cancer.

The pharmaceutical composition of the present invention may include a pharmaceutically acceptable carrier in addition to the active ingredient. Here, examples of such pharmaceutically acceptable carriers are conventionally used in formulation, and include lactose, dextrose, sucrose, sorbitol, mannitol, starch, acacia, gum, calcium phosphate, alginate, gelatin, calcium silicate, microcrystalline cellulose, polyvinyl pyrrolidone, cellulose, water, syrup, methyl cellulose, methylhydroxybenzoate, propyl hydroxybenzoate, talc, magnesium stearate, and mineral oil, but the present invention is not limited thereto. In addition, the pharmaceutical composition of the present invention may further include a lubricant, a wetting agent, a sweetener, a flavoring agent, an emulsifier, a suspending agent, and a preservative in addition to the above components.

The pharmaceutical composition of the present invention may be administered orally or parenterally (e.g., intravenously, subcutaneously, intraperitoneally, or topically) according to a desired method. However, since the composition of the present invention is easily absorbed through interaction with the LRP receptor expressed in endothelial cells of the small intestine, most preferably, it may be administered orally. For oral administration, when the active ingredient of the present invention is formulated into tablets, capsules, chewable tablets, a powder, a liquid, or a suspension, a binder such as gum arabic, corn starch, microcrystalline cellulose or gelatin, an excipient such as dicalcium phosphate or lactose, a disintegrant such as alginic acid, corn starch or potato starch, a lubricant such as magnesium stearate, a sweetener such as sucrose or saccharin, and a flavoring agent such as peppermint, methyl salicylate, or a fruity flavor may be included. When the unit dosage form is a capsule, in addition to the above ingredient, a liquid carrier such as polyethylene glycol or fatty oil may also be included.

The pharmaceutical composition of the present invention is administered at a pharmaceutically effective amount. The "pharmaceutically effective amount" used in the present invention refers to an amount applicable for medical treatment, and an effective dosage may be determined by parameters including the type and severity of a patient's disease, drug activity, sensitivity to a drug, administration time, an administration route and an excretion rate, the duration of treatment and drugs simultaneously used, and other parameters well known in the medical field. The pharmaceutical composition according to the present invention may be administered separately or in combination with other therapeutic agents and may be sequentially or simultaneously administered with a conventional therapeutic agent, or administered in single or multiple dose(s). In consideration of all of the above-mentioned parameters, it is important to achieve the maximum effect with the minimum dose without side effects, and such a dose may be easily determined by one of ordinary skill in the art.

In the present invention, the pharmaceutical composition for preventing or treating cancer may be administered alone or in combination with another anticancer agent, and when administered in combination, the order of administration is not particularly limited, and it may be administered simultaneously or sequentially with other anticancer agents.

Advantageous Effects

A glycyrrhizin-branched PEG conjugate according to one embodiment of the present invention can exhibit an excellent anticancer effect compared to glycyrrhizin and has an increased half-life in blood, so it can be effectively used for cancer treatment.

Modes of the Invention

Figure 1:
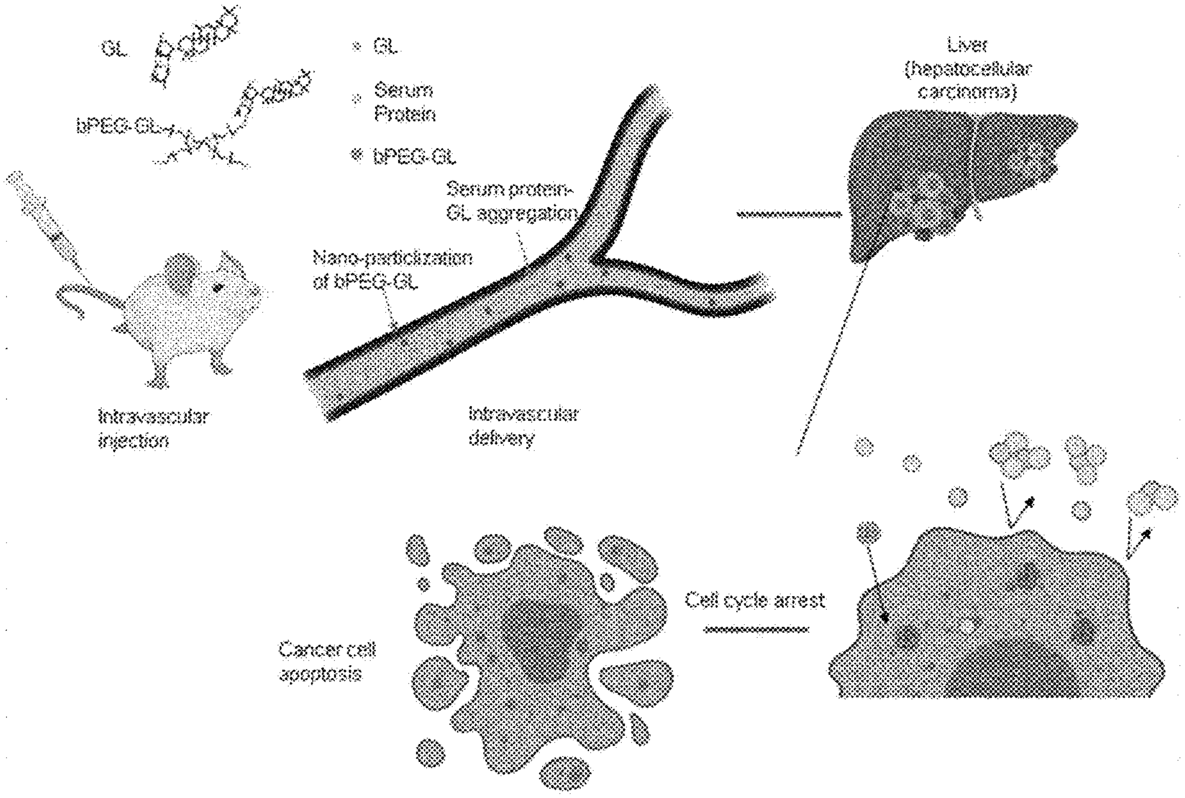
FIG. 1 shows the idea of killing hepatocellular carcinoma with a glycyrrhizin-branched PEG conjugate according to the present invention.

Hereinafter, one or more embodiments will be described in further detail with reference to examples. However, these examples are merely provided to illustrate one or more embodiments, and the scope of the present invention is not limited the following examples.

Example 1: Synthesis of Branched PEG-Glycyrrhizin

Glycyrrhizin (GL) was dissolved in distilled water (DW) at a concentration of 2 mM, and an equal volume of a sodium periodate solution dissolved in DW at 2 mM was added to the GL solution. The reactants were allowed to react for 30 minutes to prepare oxidized GL (oGL) including an aldehyde. Afterward, it was dialyzed for two days using a 1,000 Da molecular weight cut-off (MWCO) membrane, frozen in a deep freezer, and freeze-dried for two days.

The oGL was dissolved in DW at a concentration of 1 mM, and branched polyethylene glycol (PEG, 4-arm PEG-amine (2 kDa); hereinafter referred to as bPEG) dissolved in DW at a concentration of 5 mM was mixed in a molar ratio of bPEG:GL=1:4. The solution was adjusted to pH 4.5, 6.5, 9.5, or 10.5, and allowed to react at room temperature for 2 hours.

After the reaction, sodium cyanoborohydride ($NaBH_3CN$) was added at 1/1000 the volume of the bPEG-GL solution at 4° C., and a reduction reaction was performed for 20 hours. After the reaction, the resulting solution was dialyzed with 3,000 Da MWCO Centricon, and then freeze-dried.

Figure 2:
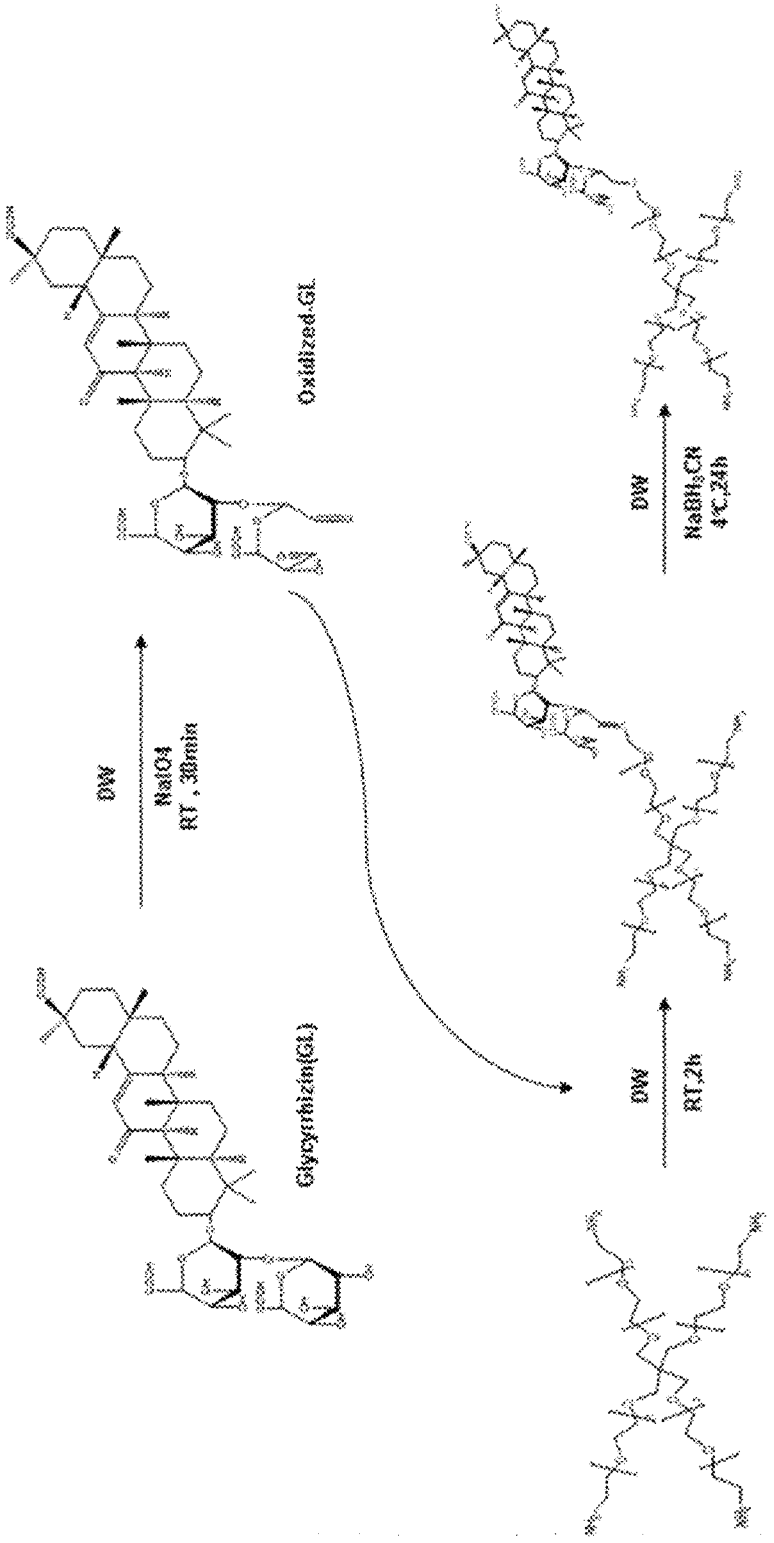
FIG. 2 shows the process of preparing a glycyrrhizin-PEG conjugate by conjugating glycyrrhizin and branched PEG (4arm-PEG-NH2).

The process of synthesizing a branched PEG-GL conjugate is shown in FIG. 2.

Example 2: Confirmation of Conjugation, Conjugation Ratio, and Size of Branched PEG-GL 2-1. H-NMR The spectra of glycyrrhizin, bPEG, and branched PEG-glycyrrhizin (bPEG-GL) synthesized by Schiff base pH conditions were measured using 500 Hz H-NMR.

Figure 3A:
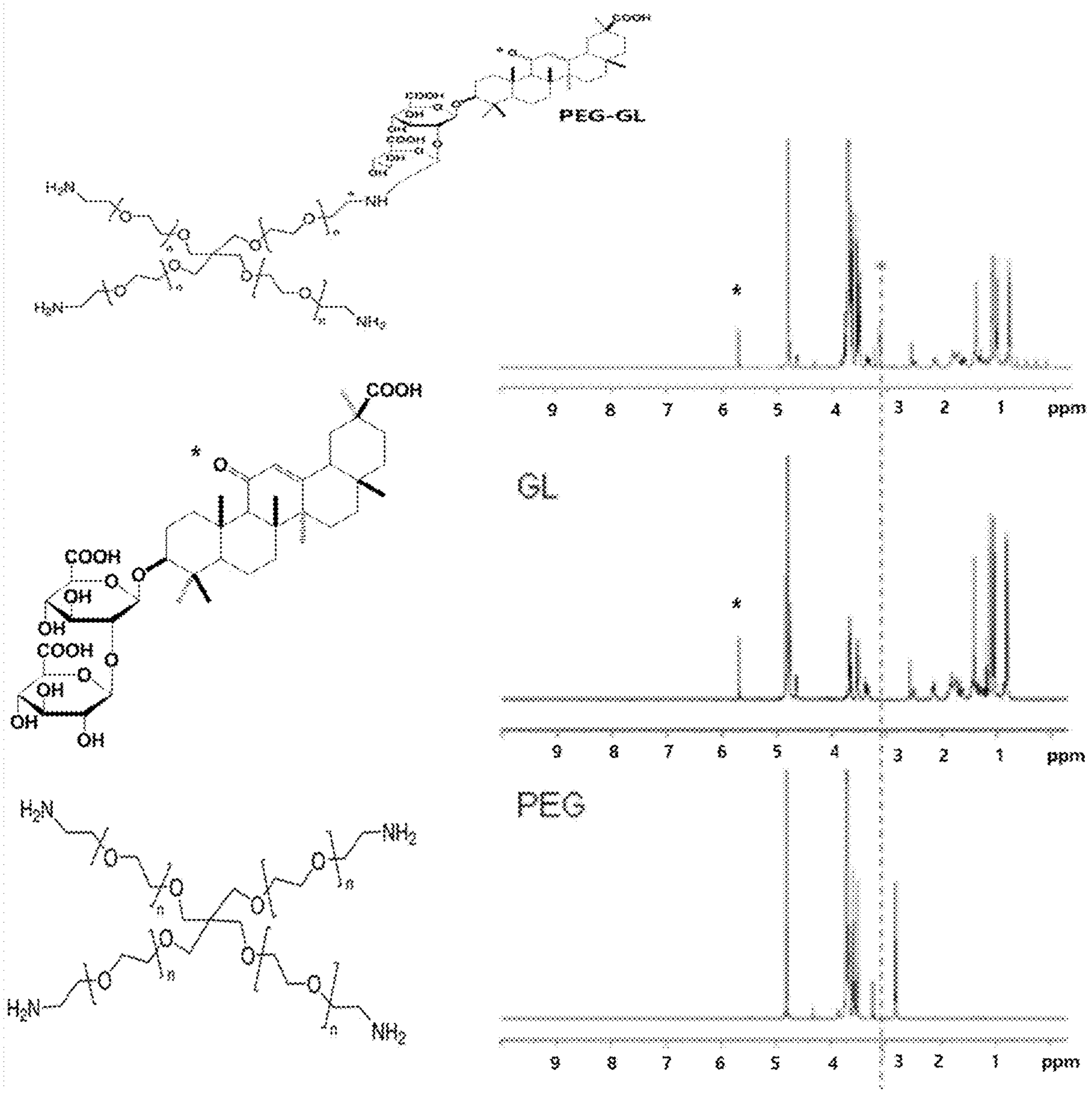
FIGS. 3A and 3B show the results of measuring the spectra of glycyrrhizin (GL), PEG, and a glycyrrhizin-PEG conjugate (bPEG-GL) using 500 Hz H-nuclear magnetic resonance (NMR).
Figure 3B:
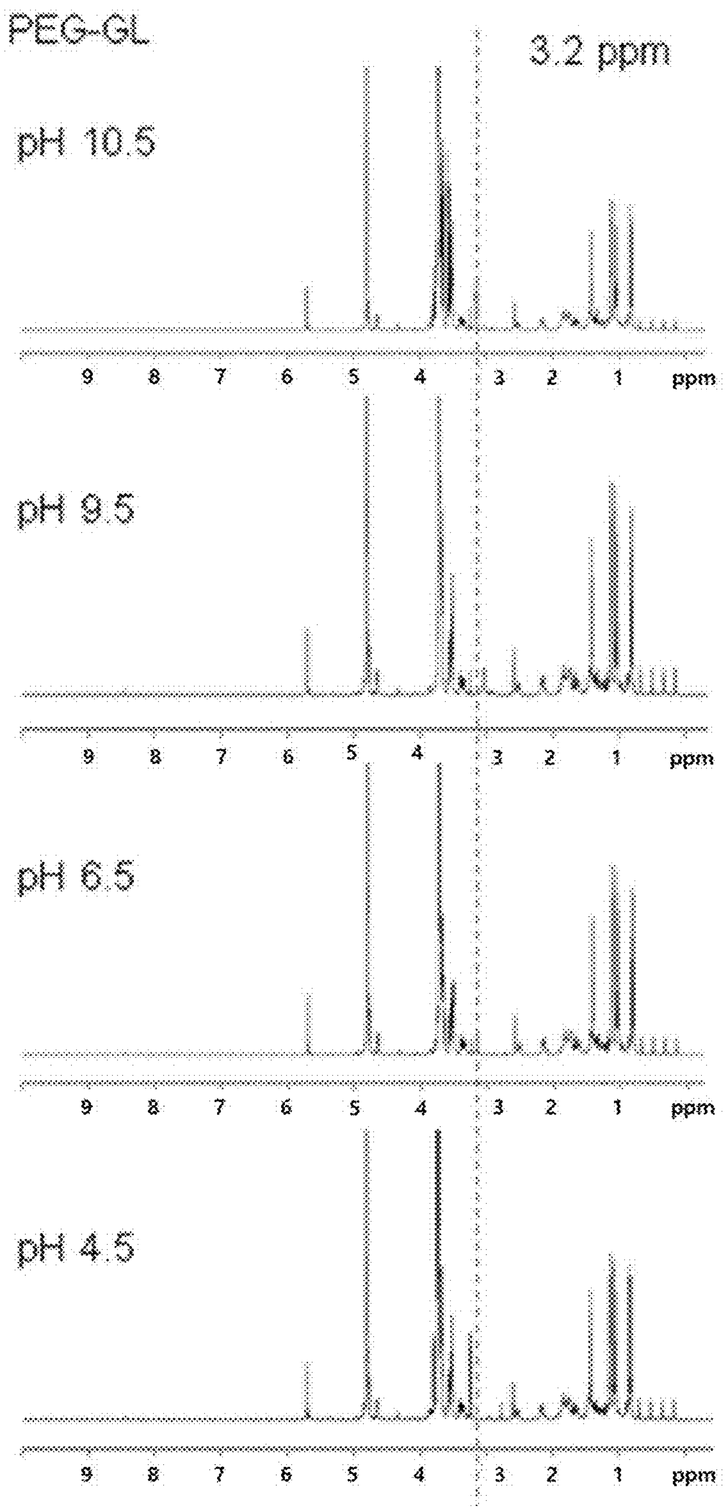
Figure 4:
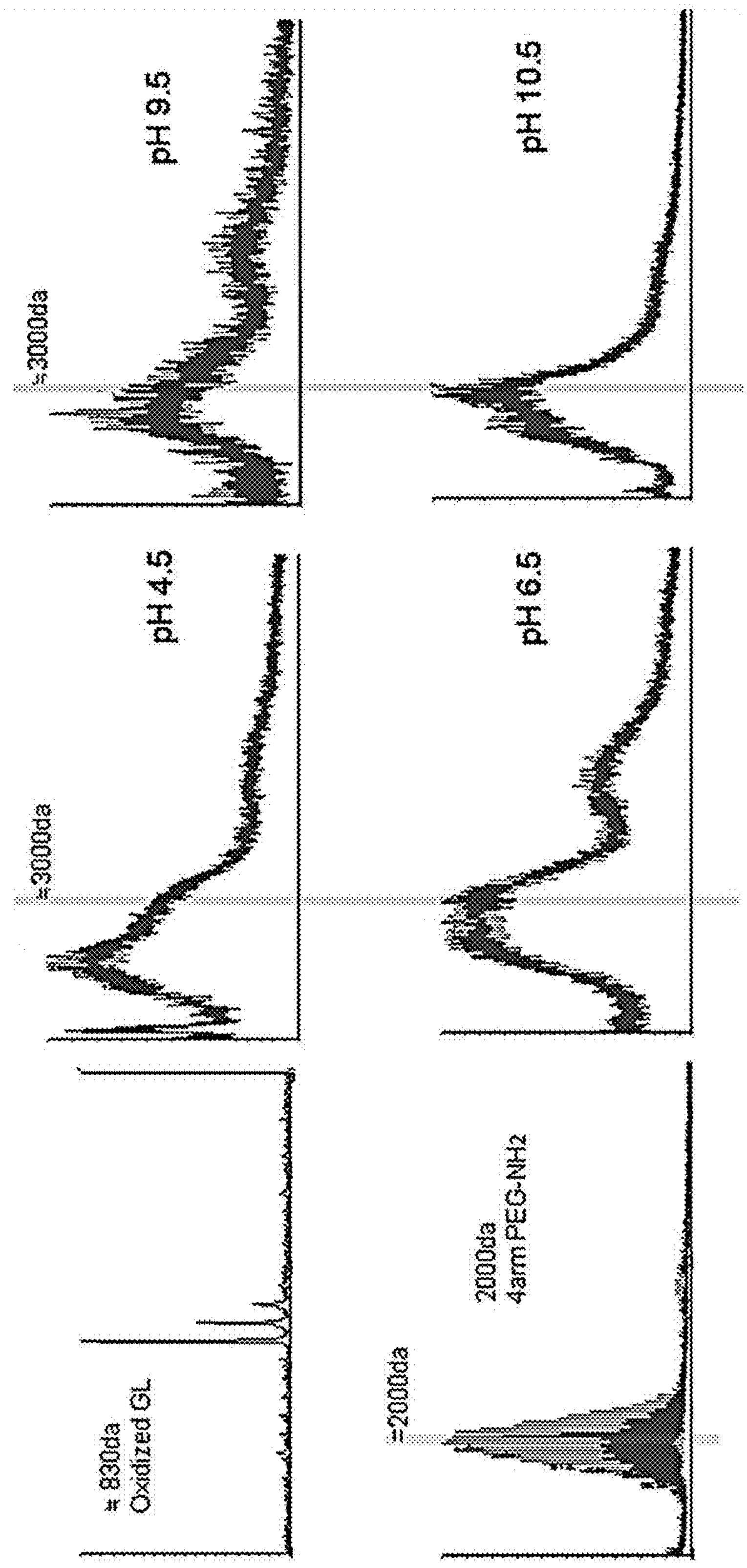
FIG. 4 shows the results of confirming the molecular weights of glycyrrhizin (GL), PEG, and a glycyrrhizin-PEG conjugate (bPEG-GL) using a matrix-assisted laser desorption/ionization time-of-flight (MALDI-TOF) mass spectrometer.

As a result, it was confirmed that the C═O peak in the GL backbone was detected at 5.8 ppm (marked by a blue asterisk in FIGS. 3A and 3B), and the proton peak of the carbon next to the primary amine of PEG was detected at 2.8 ppm (marked by a red asterisk in FIGS. 3A and 3B).

As a result of the measurement of the bPEG-GL spectrum, at pH 10.5, the proton peak of the carbon next to the secondary amine newly produced was observed at 3.2 ppm (FIGS. 3A and 3B). This result means that the branched PEG-GL conjugates were synthesized under the pH 10.5 condition.

2-2. MALDI-TOF

As a result of MALDI-TOF analysis, it was confirmed that oGL had a molecular weight of approximately 830 Da and bPEG had a molecular weight of approximately 2,000 Da. When the molecular weight of the branched PEG-glycyrrhizin synthesized under various pH conditions was analyzed, a molecular weight of approximately 3,000 Da was detected at pH 10.5, confirming that synthesis was achieved at pH 10.5.

2-3. HPLC

To confirm the conjugation ratio of oGL and bPEG, the standard curve of glycyrrhizin (GL) and glycyrrhetinic acid (GA) was plotted through HPLC using a C8 column. Specifically, a standard curve was plotted from the starting concentration of 80 μg/mL (GL): 20 μg/mL (GA) to 2.5 μg/mL (GL): 0.625 μg/mL (GA) by ½ dilution.

Figure 5A:
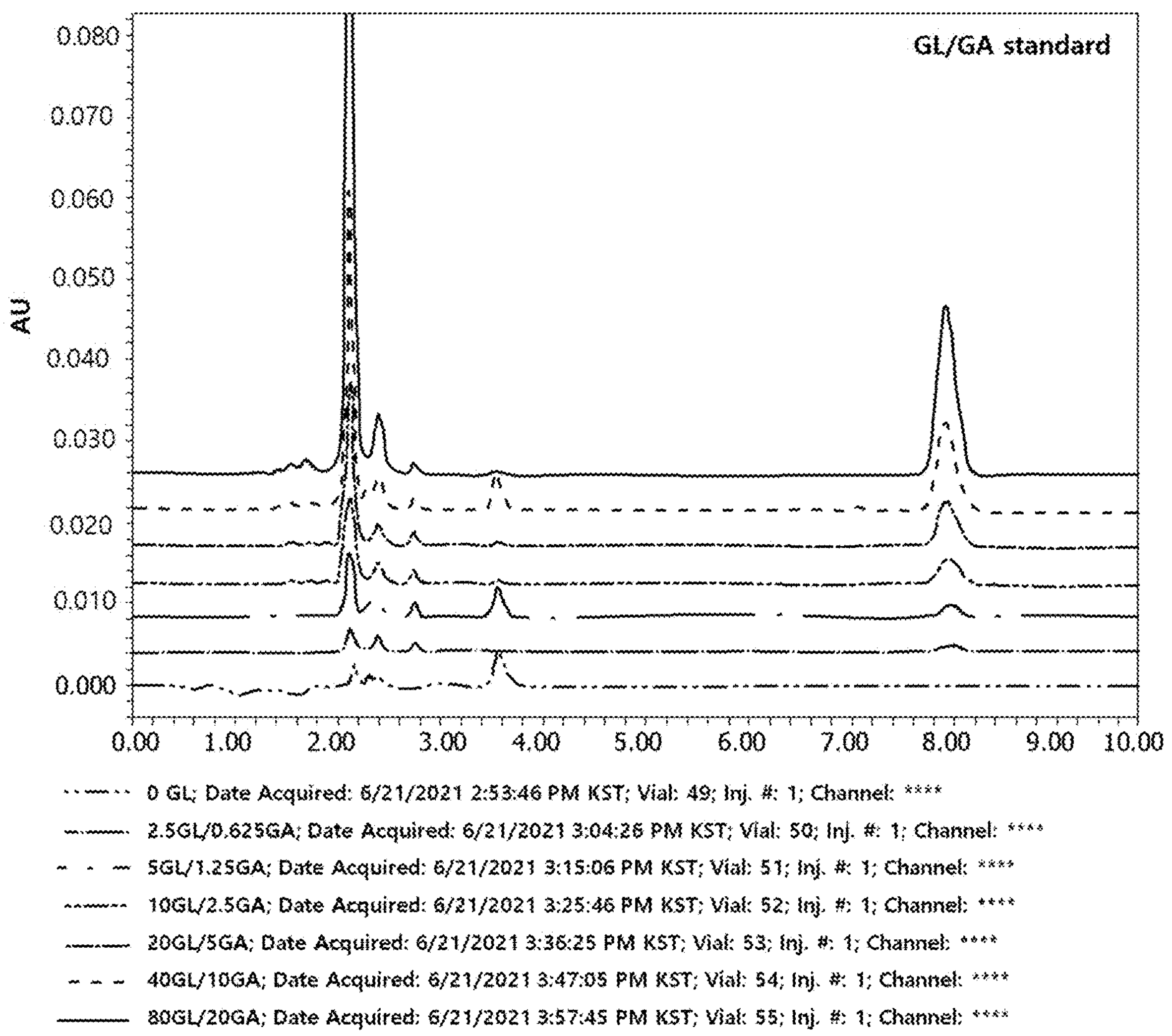
FIGS. 5A to 5C show the results of calculating the amount of glycyrrhizin in a glycyrrhizin-PEG conjugate (bPEG-GL) to confirm the conjugation ratio of glycyrrhizin and branched PEG (bPEG).
Figure 5B:
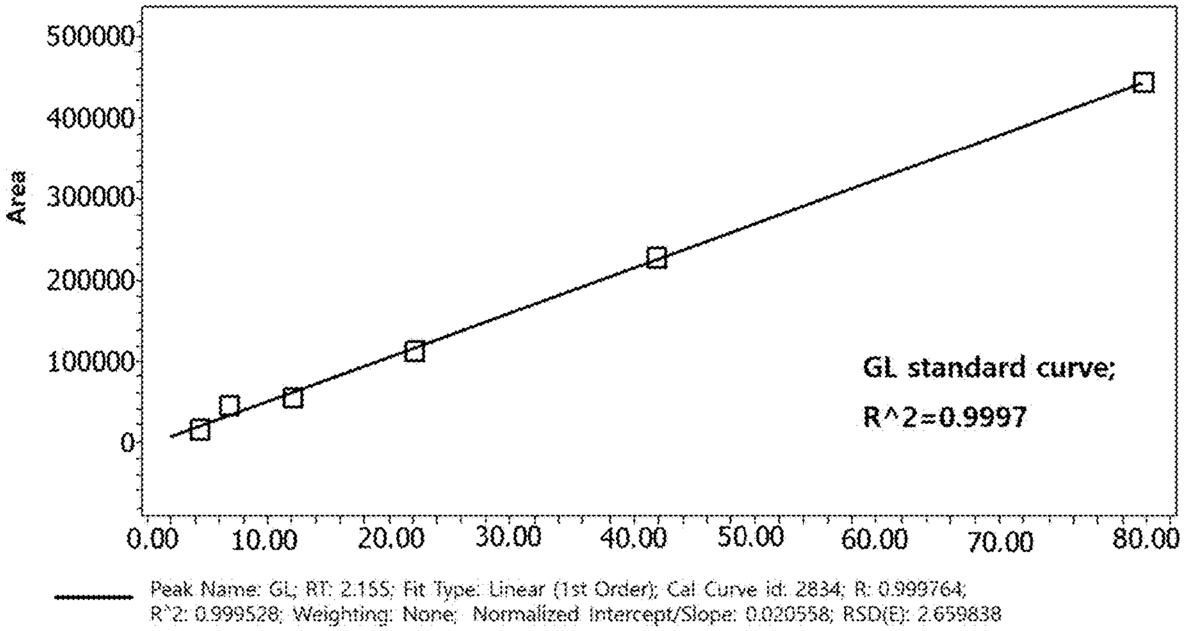
Figure 5C:
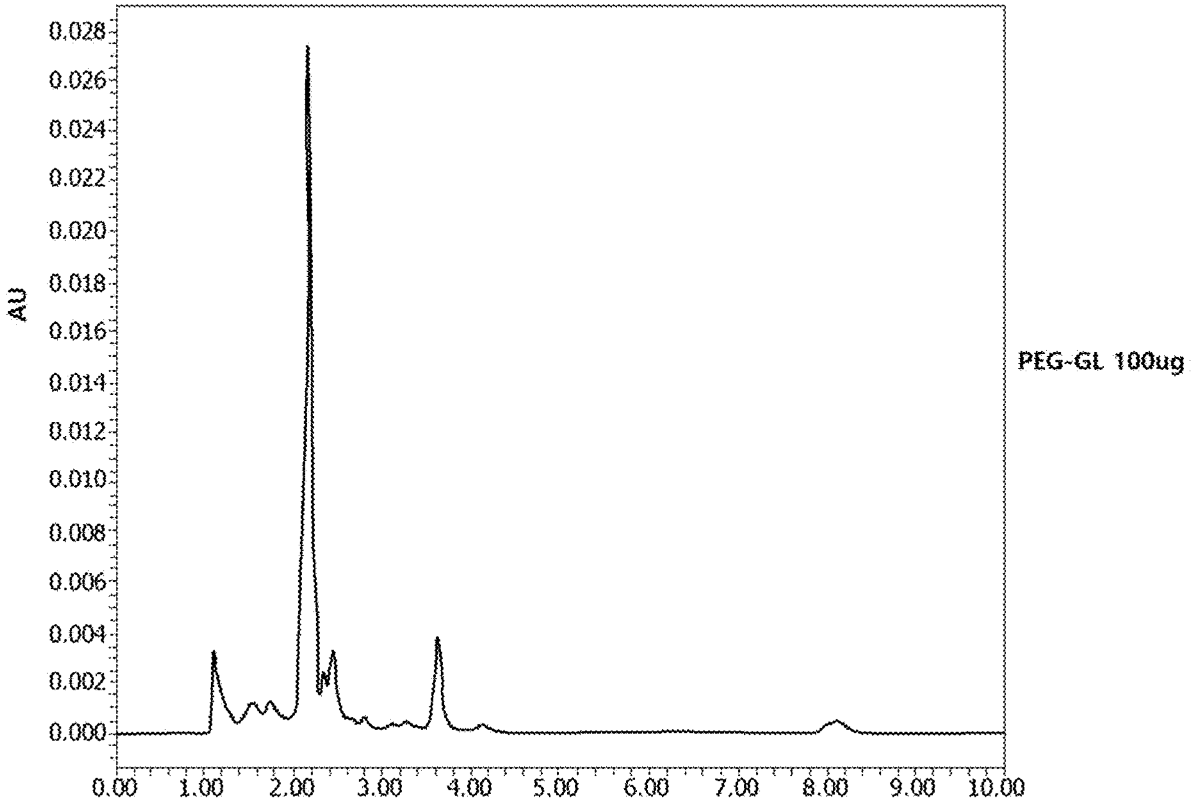

Based on the standard curve, when 100 μg of bPEG-GL was measured by HPLC to calculate a GL content, it was confirmed that 27 μg of GL was contained (FIGS. 5A to 5C). This result means that oGL and bPEG are bound at a 1:1 molar ratio, as calculated from the molecular weight value obtained from MALDI-TOF.

2-4. Confirmation of Size of Branched PEG-GL

Figure 6:
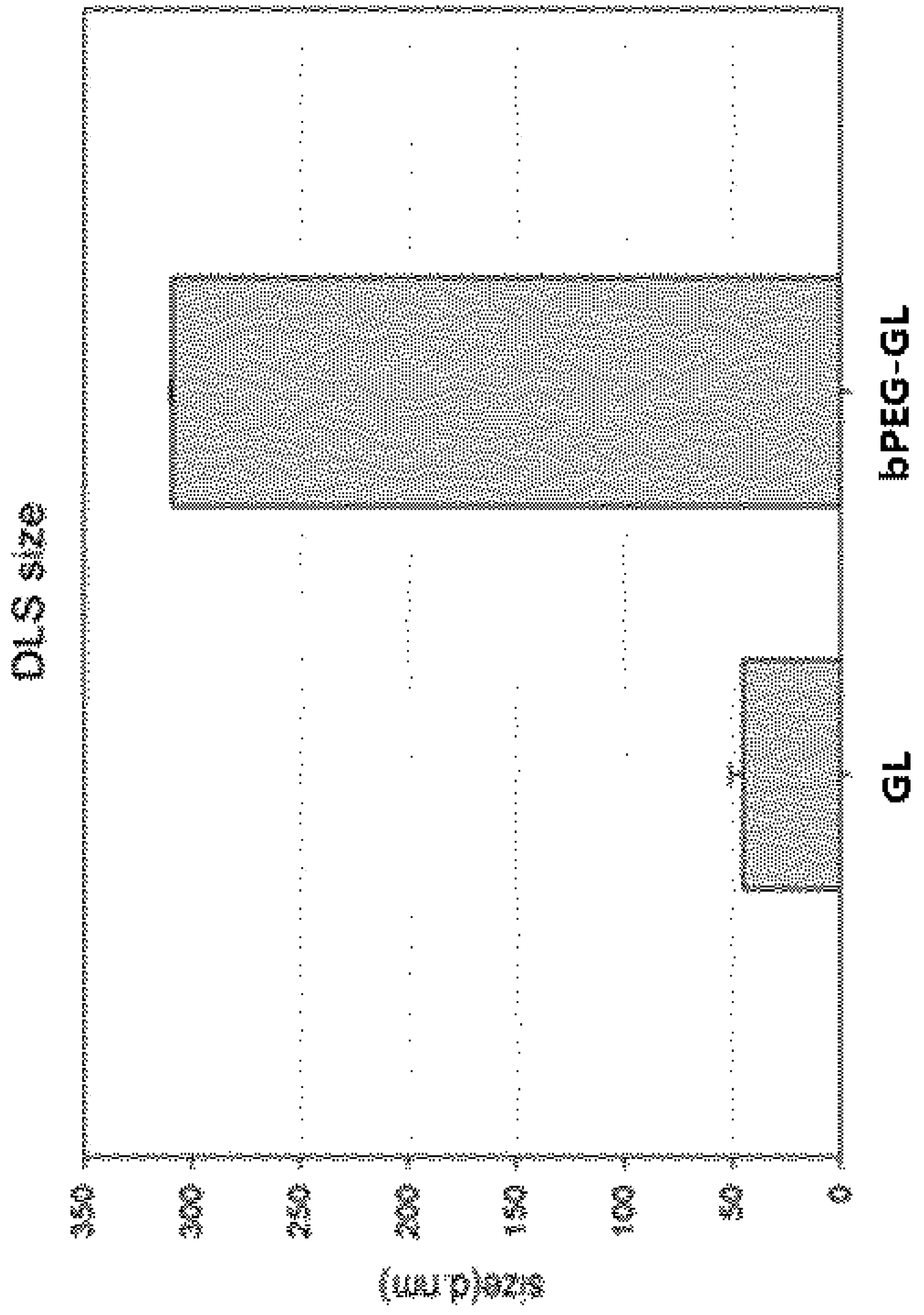
FIG. 6 shows the results of measuring the sizes of glycyrrhizin (GL) and a glycyrrhizin-PEG conjugate (bPEG-GL) using a dynamic light scattering particle size analyzer.

When measuring the size of GL using a dynamic light scattering (DLs) particle size analyzer, it was found to be 50 nm. When bPEG was conjugated, a stabilized nano size of approximately 300 nm was observed (FIG. 6).

As a result of measuring the size over time in DW in which 10% FBS was dissolved, after 1 hour, particles having a size of approximately 300 nm, which had not been previously found in the GL sample, were observed, but it was confirmed that the size of bPEG-GL was not significantly change over time (Table 1).

TABLE 1

| | | | | | | | | |
|---|---|---|---|---|---|---|---|---|
| Shielding effect check by DLS size in 10% FBS DW | | | | | | | | |
| | FBS 10% DW (control) | | | | | | | |
| Experimental | 175 nm | | 64.5% | | 17.2 nm | | 29.6% | |
| Group | 30 min | | | | 1 h | | | |
| GL | 159.7 nm | 75.50% | 10.38 nm | 24.15% | 54.5 nm | 47.83% | 295.03 nm | 31.06% |
| bPEG-GL | 315.07 nm | 41.60% | 44.10 nm | 37.80% | 308.1 nm | 42.87% | 41.44 nm | 36.40% |

Example 3: Confirmation of Toxicity and Cellular Uptake of Branched PEG-GL

3-1. Cytotoxicity

Human umbilical vein endothelial cells (HUVECs), which are vascular epithelial cells, HepG2 cells, which are liver cancer cells, and HEK-293T cells, which are renal cells were seeded in a 96-well plate at $1\times10^4$ cells/well and cultured for 24 hours. Afterward, bPEG-GL was treated at an equivalent concentration based on a preset treatment concentration of GL. That is, bPEG-GL was treated so that the amount of glycyrrhizin was the same. Likewise, the concentration of bPEG to be treated at each bPEG-GL concentration was calculated and treated. After 24-hr culture, a cytotoxicity level was assessed through CCK-8 assay.

Figure 7A:
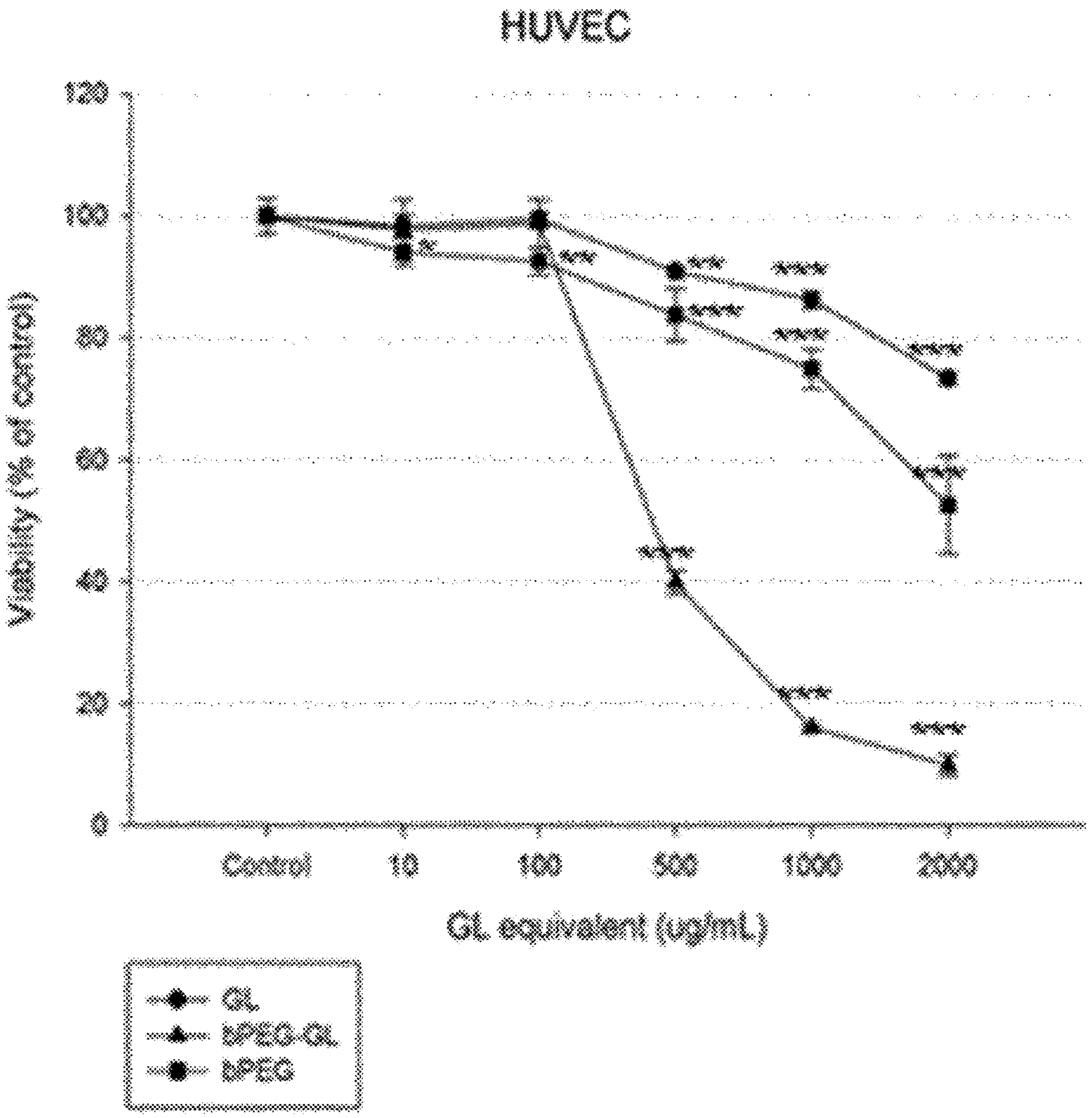
FIGS. 7A and 7C show the results of confirming the degree of cytotoxicity after treating HUVECs, HepG2 cells, and HEK-293T cells with glycyrrhizin (GL), PEG and a glycyrrhizin-PEG conjugate (bPEG-GL). The data was expressed as mean ±S.D. (n=5). Compared to a control, * indicates $p<0.05$,  indicates $p<0.01$, and * indicates $p<0.001$.

In HUVECs, at a concentration of 500 μg/mL or more, it can be confirmed that bPEG-GL exhibited higher cytotoxicity than GL (FIG. 7A), indicating that bPEG-GL has higher efficiency in inhibiting angiogenesis.

Figure 7B:
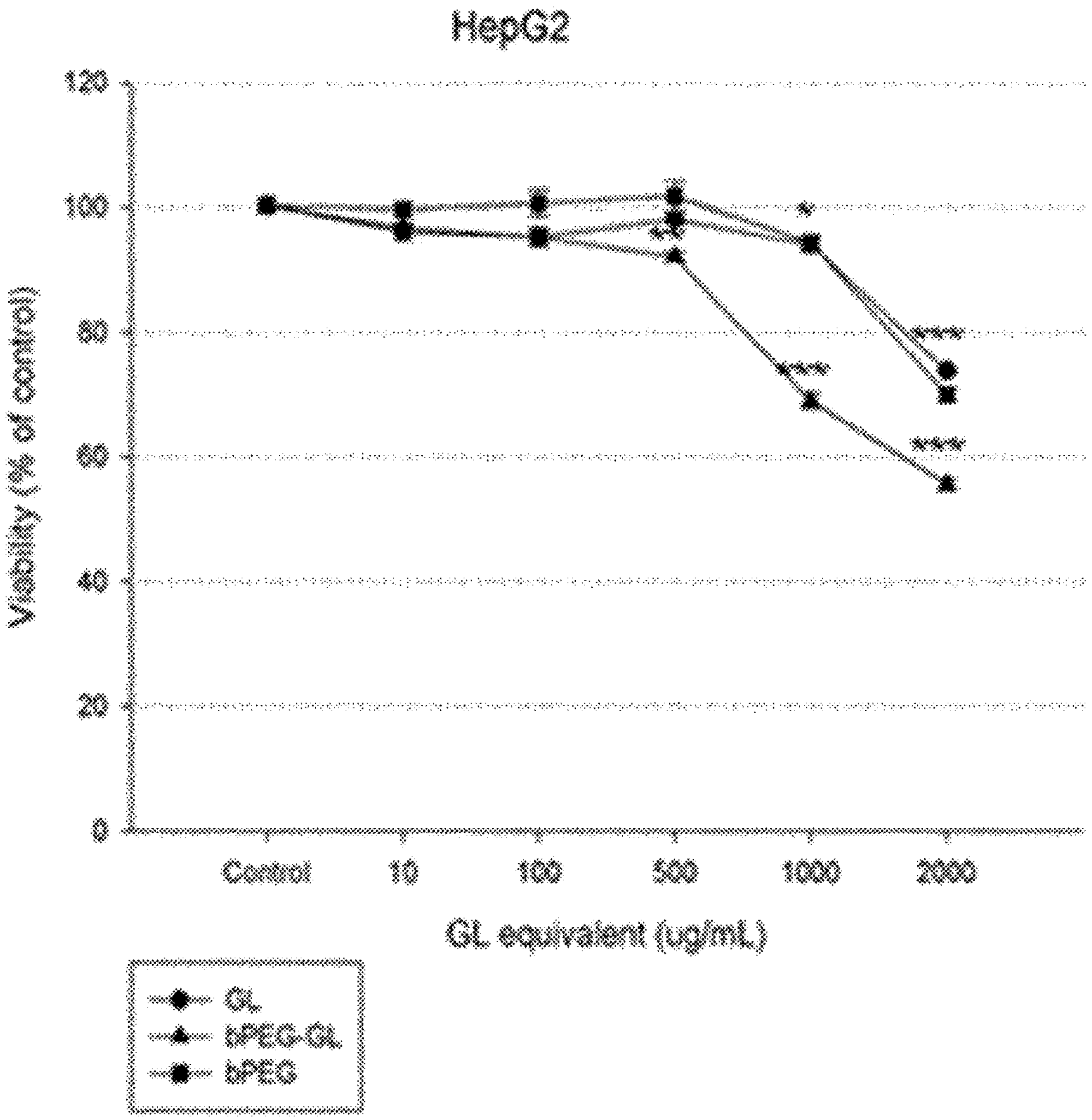

In HepG2 cells, bPEG-GL exhibited higher cytotoxicity than GL at concentrations of 500 μg/mL or more (FIG. 7B), indicating that the anticancer effect of bPEG-GL is better than that of GL.

Figure 7C:
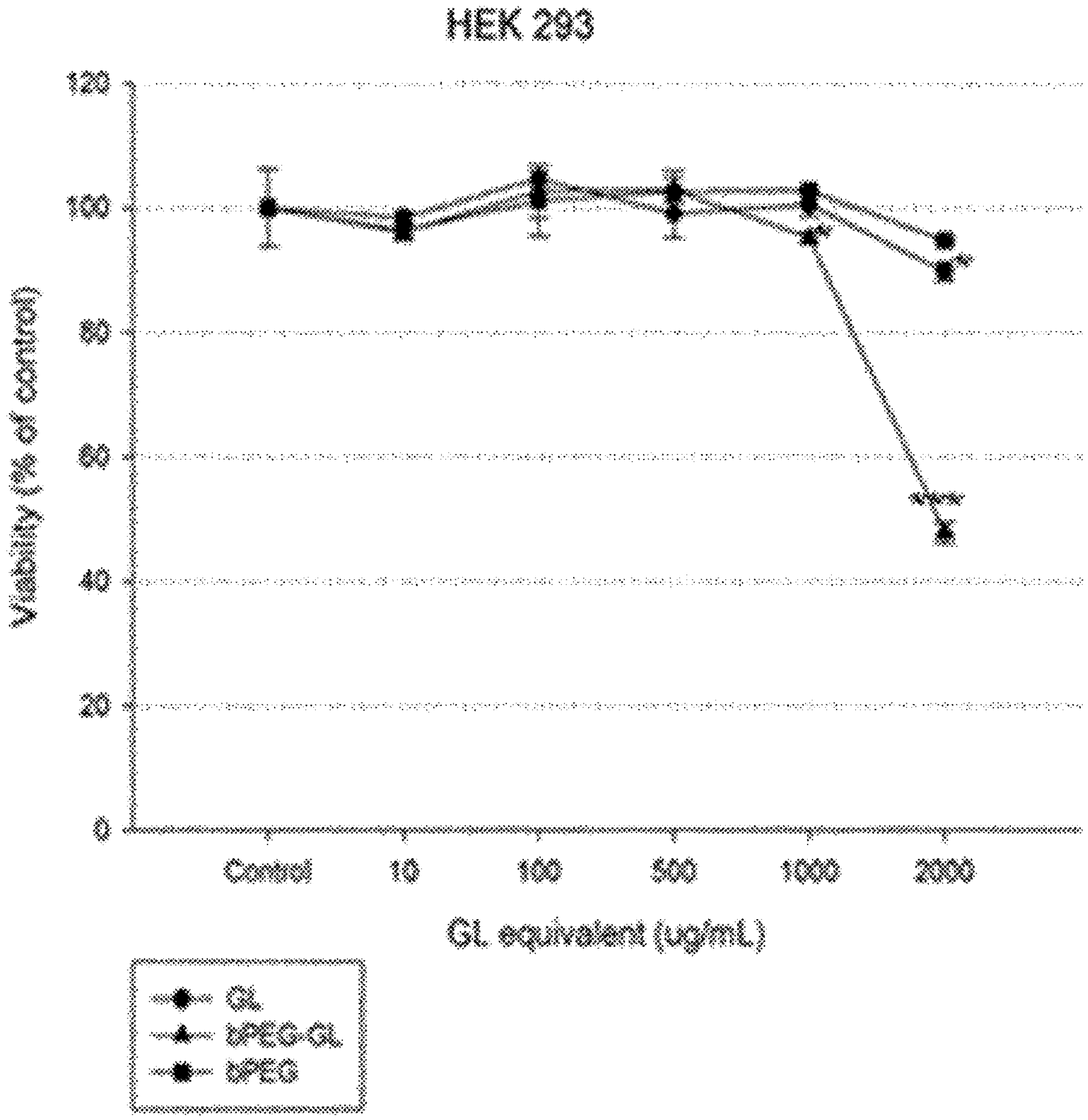

In the normal cells, HEK-293T cells, as a comparative experimental group, toxicity was not exhibited in all experimental groups up to 1 mg/mL (FIG. 7C).

3-2. In Vitro Blood Hemolysis

Since bPEG-GL was shown to be highly toxic to vascular cells at high concentrations (1.8 mg/mL) (FIG. 7A), the toxicity to blood cells was confirmed.

1 to 2 mL of blood was put into a 2 mL tube, filled with PBS, and centrifuged at 3,000 rpm for 2 minutes. The supernatant was removed, the vial was filled again with PBS, and centrifuged, and this process was repeated 2 to 3 times. 20 μL of a red blood pellet was dispensed into a 1.5 mL tube. DW, for example, 80% DW/PBS, 60% DW/PBS, 40% DW/PBS, 20% DW/PBS, or PBS was added to a control without separate material treatment, and the volumes was adjusted to 1.5 mL. In the experimental group, 1 mL of a bPEG-GL (3.6 mg/mL, 2.88 mg/mL, 2.16 mg/mL, 1.44 mg/mL, 0.72 mg/mL; GL equivalent concentration) solution was added to each tube.

The tubes were left in a 37° C. water bath for 1 hour and then centrifuged at 800 rpm for 5 minutes. Whether hemolysis of red blood cells occurred was observed with the naked eye, and the UV absorbance of the supernatant was measured at 420 nm using NanoDrop.

Figure 8:
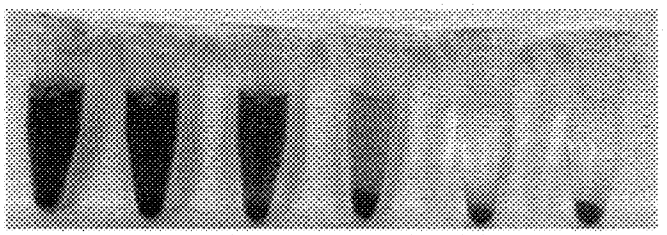
FIG. 8 shows the results of confirming whether hemolysis occurs after mixing blood cells with glycyrrhizin (GL) or a glycyrrhizin-PEG conjugate (bPEG-GL).
Figure 8:
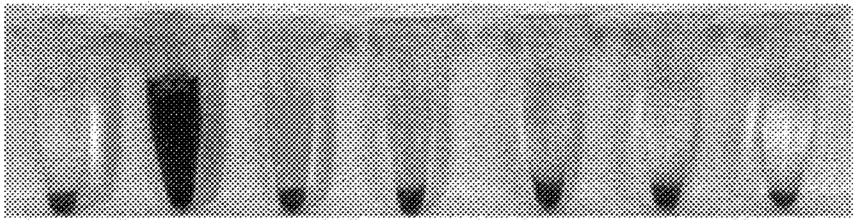
Figure 8:
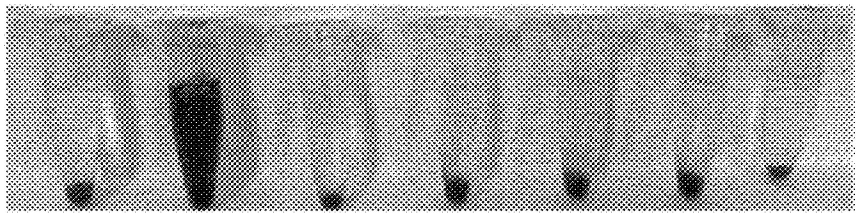

As a result of measurement, it was confirmed that both GL (0.2 to 1 mg/mL) and bPEG-GL (3.6 to 0.72 mg/mL; GL equivalent concentration) did not exhibit toxicity to blood cells in the observed concentration range (FIG. 8). This result reveals that, even when bPEG-GL is delivered into the body through intravenous injection, there is no problem with blood cell toxicity.

3-3. Cellular Uptake

The cellular uptake efficiency of GL-FITC and bPEG-GL-FITC in liver cancer cell line, HepG2 cells, was qualitatively and quantitatively analyzed using flow cytometry (FACS) and confocal laser scanning microscopy (CLSM).

GL-FITC was synthesized as follows: GL was dissolved in a buffer containing 0.1 M MES (N-morpholineethanesulfonic acid) and 0.5 M NaCl at a concentration of 1 mg/mL. 8 mL of EDC (1-ethyl-3-(3-dimethylaminopropyl) carbodiimide hydrochloride) and 12 mg of NHS (N-hydroxysulfosuccinimide) were added to 20 mL of the GL solution and allowed to react at room temperature for 15 minutes. FITC was dissolved in 1 mL of DMSO at the molar amount as 20 mg of GL and PBS was added to achieve the same molar concentration, thereby preparing an FITC solution. The GL solution and the FITC solution were mixed and allowed to react at room temperature for 4 hours. It was dialyzed for 2 days using a 1000 Da MWCO membrane and then freeze-dried.

bPEG-GL-FITC was synthesized as follows: GL-FITC was dissolved in DW at a concentration of 2 mM, mixed with the same amount of 2 mM sodium periodate solution and oxidized for 30 minutes. A 5 mM bPEG solution was added to the oxidized GL-FITC solution such that the molar ratio of the oxidized GL-FITC and bPEG became 1:4, and the pH of the resulting solution was adjusted to 10.5 to allow a reaction at room temperature for 2 hours. A sodium cyanoborohydride solution was added at 1/1000 the volume of the bPEG-GL-FITC solution and reduced at 4° C. for 24 hours.

$3\times10^5$ HepG2 cells were seeded in a 60 mm culture plate and cultured for 24 hours. GL-FITC and bPEG-GL-FITC were dissolved in DMEM to have a concentration of 125 μg/mL based on the GL concentration, and HepG2 cells were with the same for 1, 3 and 5 hours. After washing the cells three times with PBS, flow cytometry was performed.

Figure 9A:
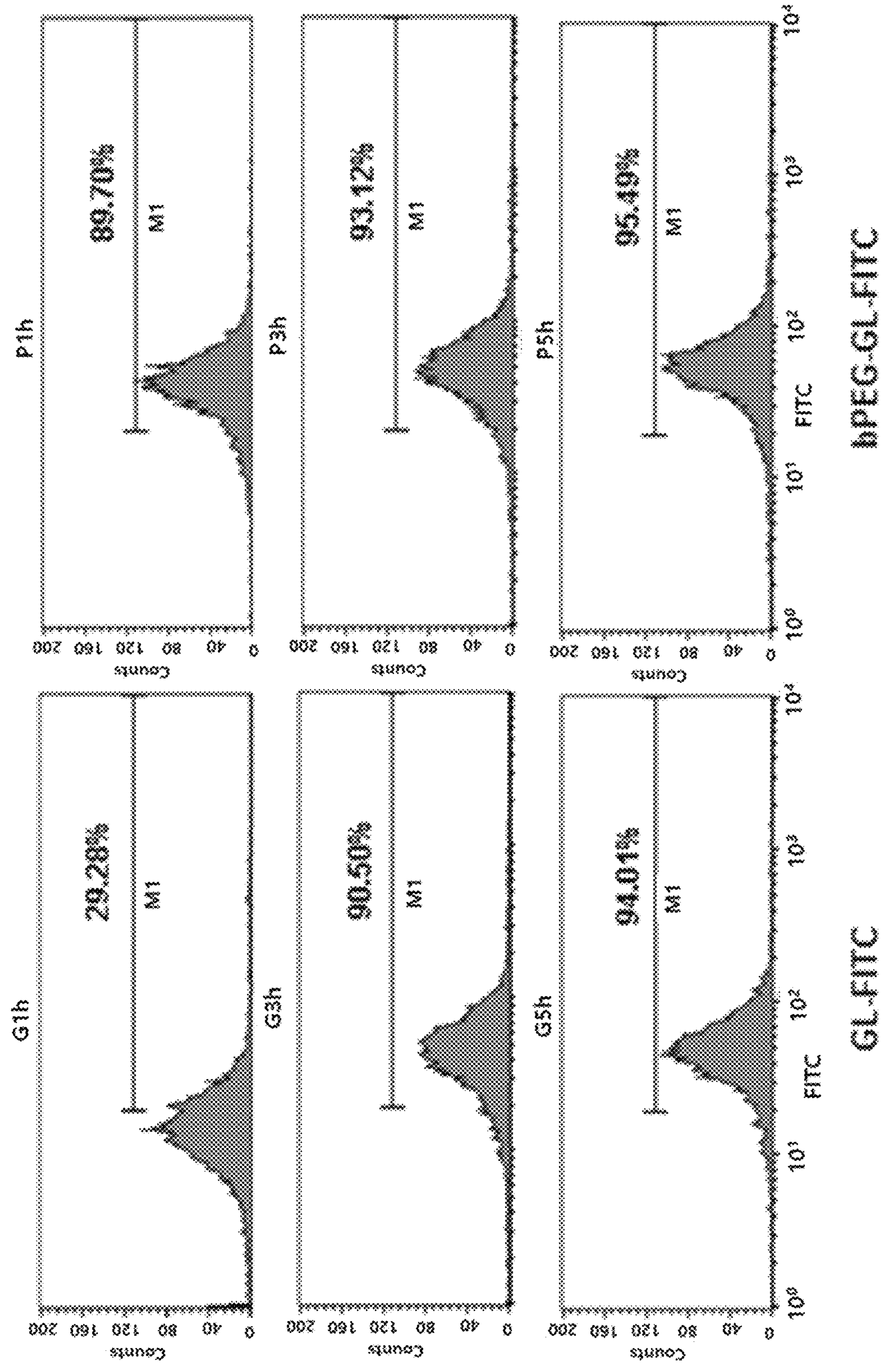
FIG. 9A shows the results of confirming the degree of intracellular uptake through flow cytometry after treating HepG2 cells with glycyrrhizin (GL) or a glycyrrhizin-PEG conjugate (bPEG-GL).

As a result, it was confirmed that the degree of cellular uptake of bPEG-GL-FITC was significantly higher than that of GL-FITC when treated for 1 hour (29.28% vs. 89.70%), and that the degree of cellular uptake of bPEG-GL-FITC was also higher at other treatment times (FIG. 9A).

HepG2 cells were seeded at $1\times10^4$ cells/well in 4-well Lab-Tek and cultured for 24 hours. GL-FITC and bPEG-GL-FITC were dissolved in DMEM to have a concentration of 125 g/mL based on the GL concentration, and FITC was dissolved in DMEM using NanoDrop to have the same UV absorbance value at 465 nm. The HepG2 cells were treated with each of GL-FITC, bPEG-GL-FITC, and FITC for 1 hour. The cells were washed with PBS three times, subjected to DAPI mounting, covered with a cover glass, and observed using a confocal microscope.

Figure 9B:
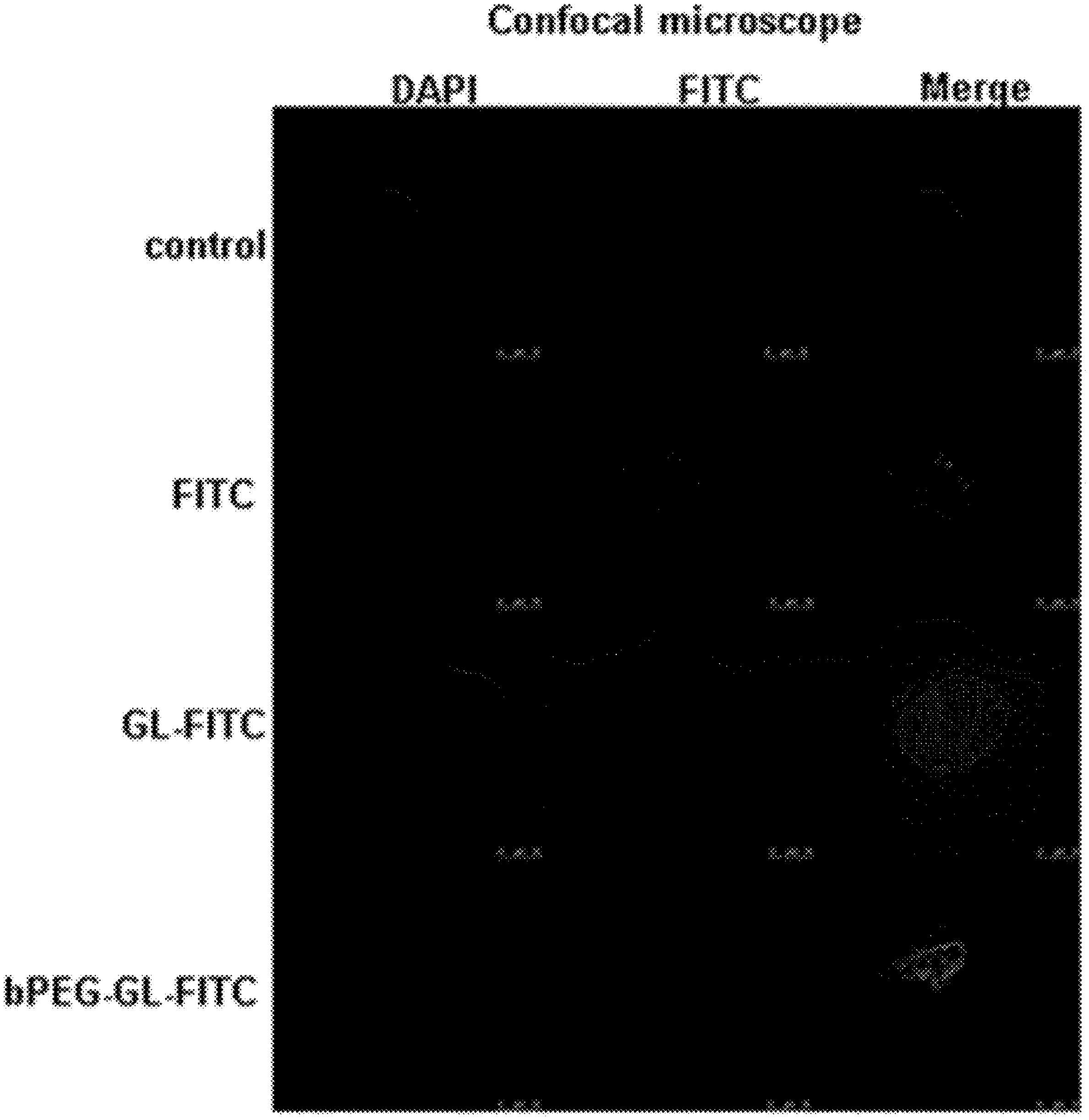
FIG. 9B shows the results of confirming the degree of intracellular uptake using a confocal microscope after treating HepG2 cells with glycyrrhizin (GL) or a glycyrrhizin-PEG conjugate (bPEG-GL).

As a result of observation, like the flow cytometry results, it was confirmed that the degree of cellular uptake of bPEG-GL-FITC was greater than that of GL-FITC (FIG. 9B).

The results in FIG. 9 show that the cellular uptake efficiency of bPEG-GL is superior to that of GL.

Example 4: Anticancer Effect of Branched PEG-GL 4-1. Wound Healing Assay

Figure 10A:
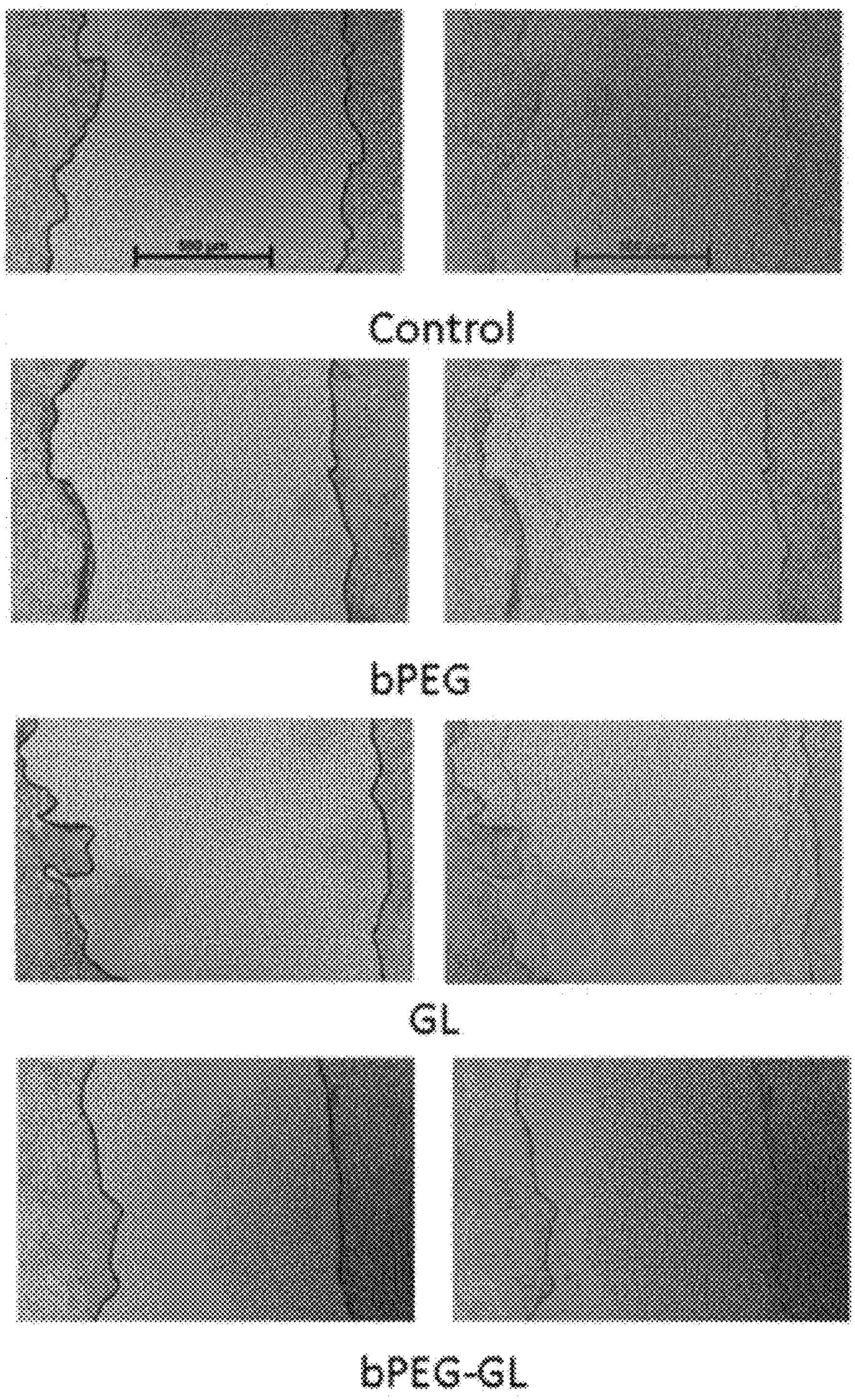
FIG. 10A shows the results of confirming the degree of wound healing after making a scratch on the surface of a HepG2 cell culture plate and treating the cells with glycyrrhizin (GL), branched PEG (bPEG), or a glycyrrhizin-PEG conjugate (bPEG-GL).
Figure 10B:
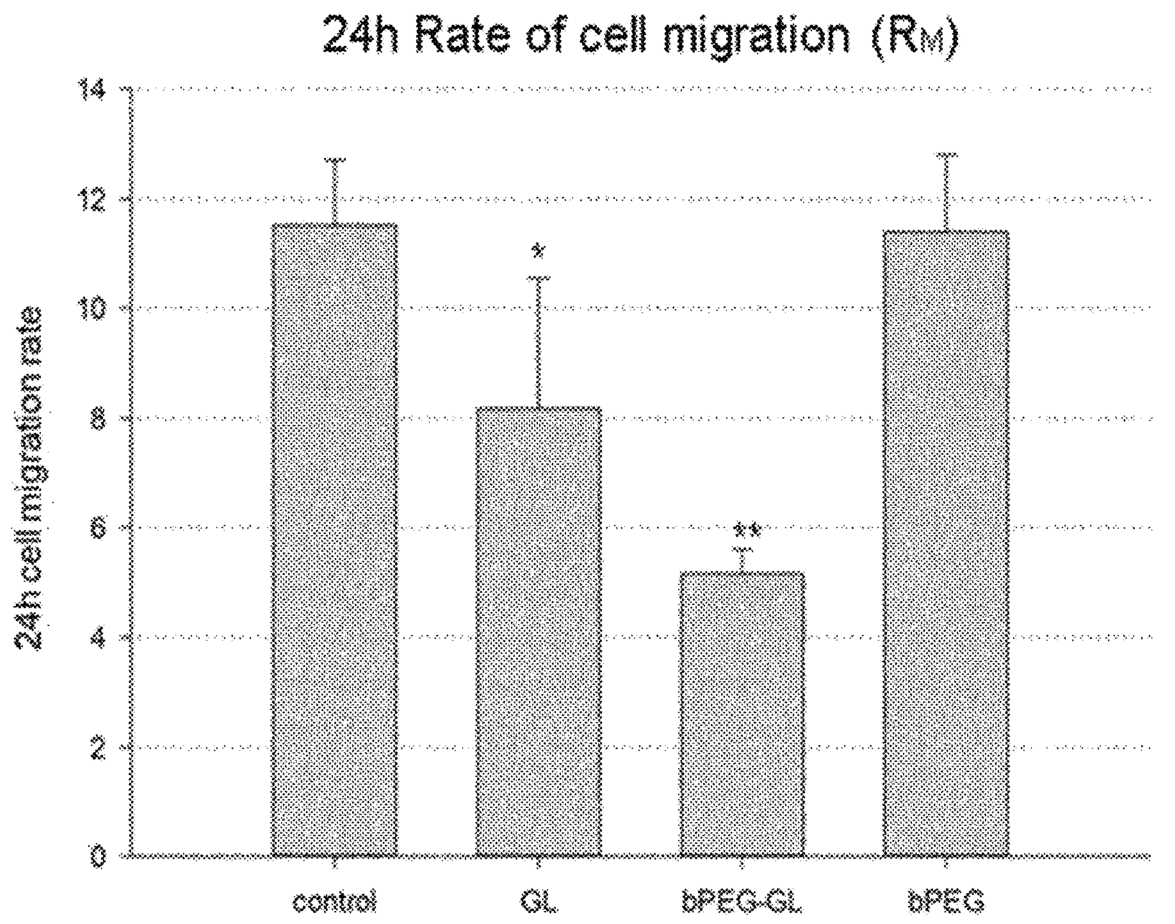
FIG. 10B is a graph showing the results of FIG. 10A.

HepG2 cells were seeded in a 6-well plate at $3\times10^5$ cells/well and cultured until 100% confluence. When the well was filled with cells, a wound was made by drawing a line in the center of the well using a 200 μL micropipette tip. The cells were washed with PBS, and treated with each of 500 μg/mL of GL, 500 μg/mL of bPEG-GL, which is a GL equivalent concentration, and a bPEG solution at the same amount of bPEG that dissolved in 500 μg/mL of bPEG-GL. After 24-hour culture, the width of the wound was confirmed. As a result, there was no significant difference in the width of the wound between the control and the bPEG-treated group, but the GL-treated group showed an inhibitory effect on cell migration, and the bPEG-GL-treated group showed an improved migration inhibitory effect compared to the GL-treated group (FIGS. 10A and 10B). The cell migration rate was calculated according to Equation 1.

$$\text{Rate of cell migration}(RM)=(Wi-Wf)/t \quad \text{[Equation 1]}$$

(Wi=initial wound width, Wf=final wound width, t=duration of migration)

4-2. Cell Cycle Arrest Assay

HepG2 cells were seeded in a 6-well plate at $4\times10^5$ cells/well and cultured (3 wells for each treated group). The cells were classified into a control (con; untreated group), GL-treated groups (250 and 500 μg/mL), bPEG-GL-treated groups (GL equi 250 and 500 μg/mL), and a bPEG (GL equi 500 μg/mL)-treated group, treated with corresponding materials, and cultured for 24 hours. After the cells were recovered and counted, $1\times10^6$ cells were obtained for each experimental group. The cells were washed with PBS and fixed with 70% ethanol (cell membrane disruption). The cells were treated with 50 μL of ribonuclease A (100 μg/mL) and 200 μL of propidium iodide (PI; 50 μg/mL). The cells were washed and suspended in 500 μL of PBS, and then FACS was performed.

Figure 11A:
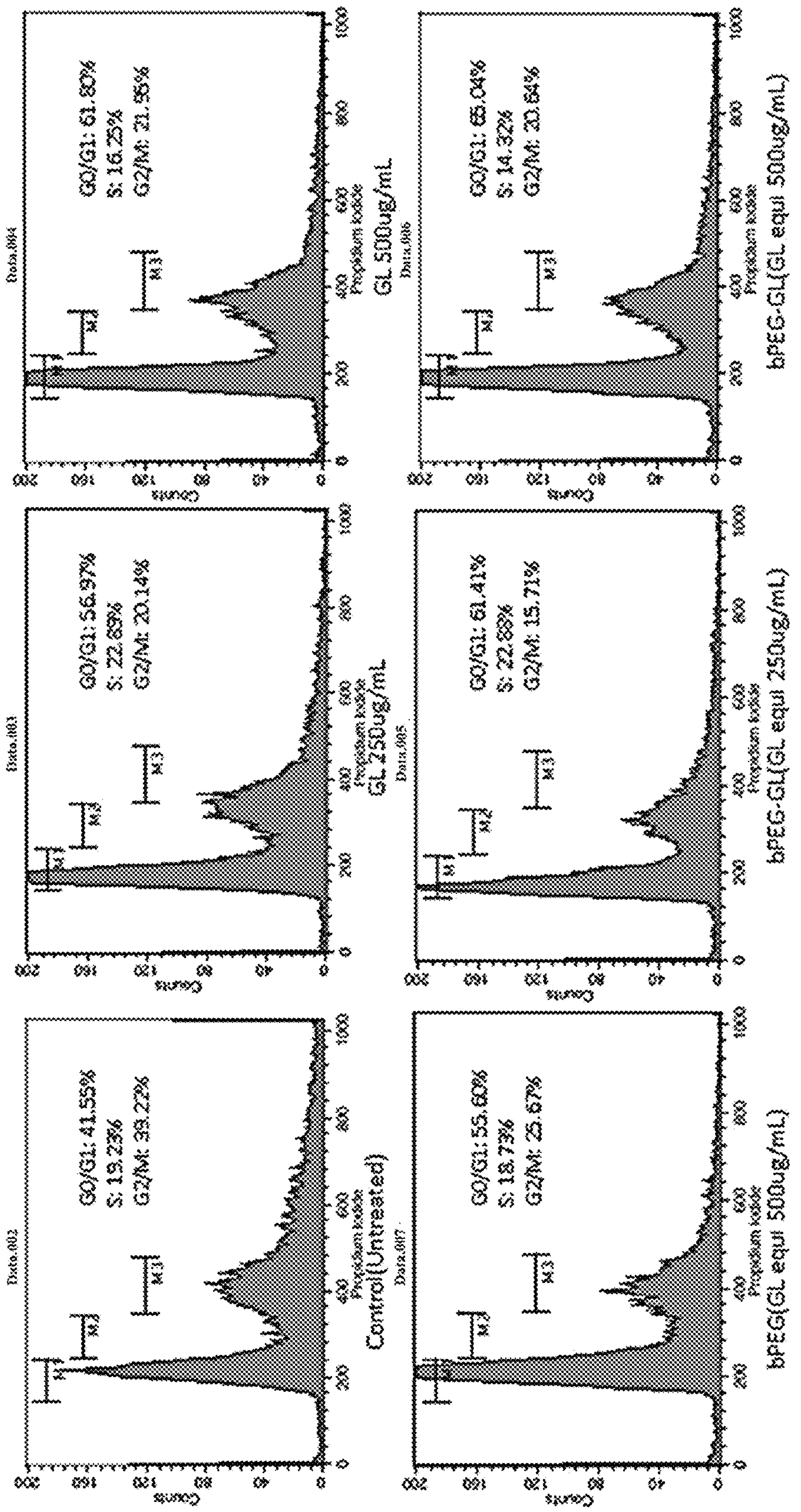
FIG. 11A shows the results of analyzing a cell cycle through flow cytometry after treating and culturing HepG2 cells with glycyrrhizin (GL), branched PEG (bPEG), or a glycyrrhizin-PEG conjugate (bPEG-GL).
Figure 11B:
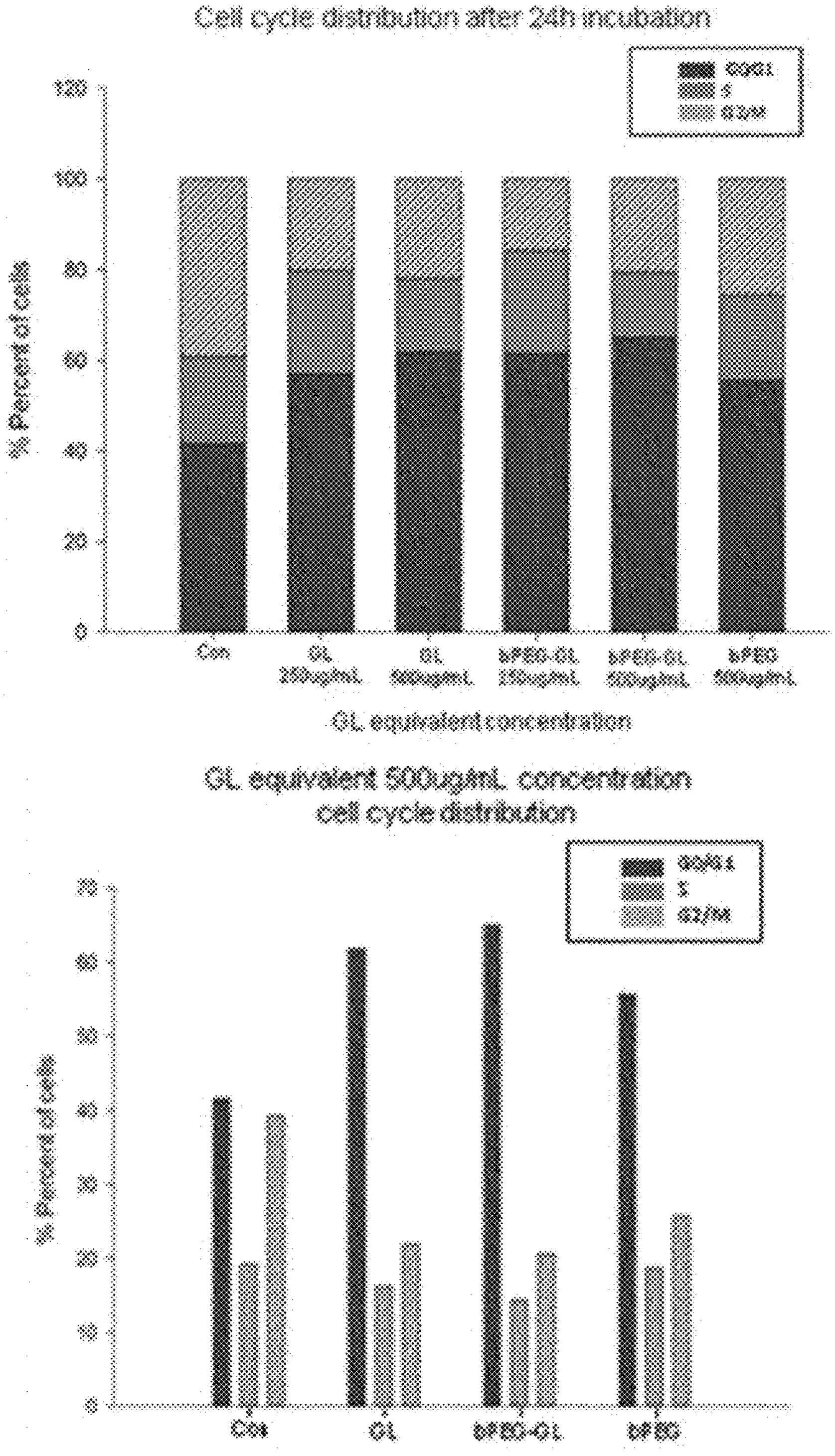
FIG. 11B is a graph showing the results of FIG. 11A.

As a result, it was confirmed that, in the control, 50% or more of the cells were in the S and G2/M phases, indicating that they had entered the cell proliferation phase, and in the GL-treated group and the bPEG-GL-treated group, the cell cycles remained in the G0/G1 phase compared to the control (S:DNA synthesis phase; G0/G1; cell growth preparation phase; and G2/M: differentiation phase). Both the GL-treated group and the bPEG-GL-treated group exhibited higher cell cycle arrest effects at 500 μg/mL, compared to that at 250 μg/mL, and at the same concentration, the proportion of cells arrested in the G0/G1 phase was higher in the bPEG-GL-treated group than the GL-treated group (FIGS. 11A and 11B).

The results of this experiment can confirm that both GL and bPEG-GL can inhibit cell proliferation, and that bPEG-G has a better cell proliferation inhibition effect.

4-3. Apoptosis Assay

To confirm the effect of GL and bPEG-GL on apoptosis, the concentration of GL that exhibits cytotoxicity was set to 1 mg/mL to perform apoptosis assay.

HepG2 cells were seeded in a 60 mm well plate at $2\times10^5$ cells/well and cultured (3 wells for each treatment group). The cells were classified as follows, treated with corresponding materials, and cultured for 24 hours: Control (con; untreated group), GL-treated groups (250, 500, and 1,000 μg/mL), bPEG-GL-treated groups (900, 1,800, and 3,600 μg/mL; GL equivalent concentrations of 250, 500, and 1,000 μg/mL), and bPEG-treated groups (1,300 and 2,600 μg/mL; bPEG-GL equivalent concentrations of 1,800 and 3,600 μg/mL).

After the culture, the medium was aspirated to remove the treated material, and the cells were washed twice with a cell-staining buffer. After the cells were recovered and counted, $5\times10^5$ cells were obtained for each experimental group. The cell culture solution was centrifuged to remove the supernatant, and then the cells were suspended in 100 μL of annexin V-binding buffer. The cell suspension was transferred to an FACS tube, and 5 μL of annexin V and 10 μL of PI solution were added. Subsequently, the FACS tube was left in a dark room at room temperature for 15 minutes. 400 μL of PBS was added to each FACS tube and analyzed by FACS in appropriate settings.

Figure 12A:
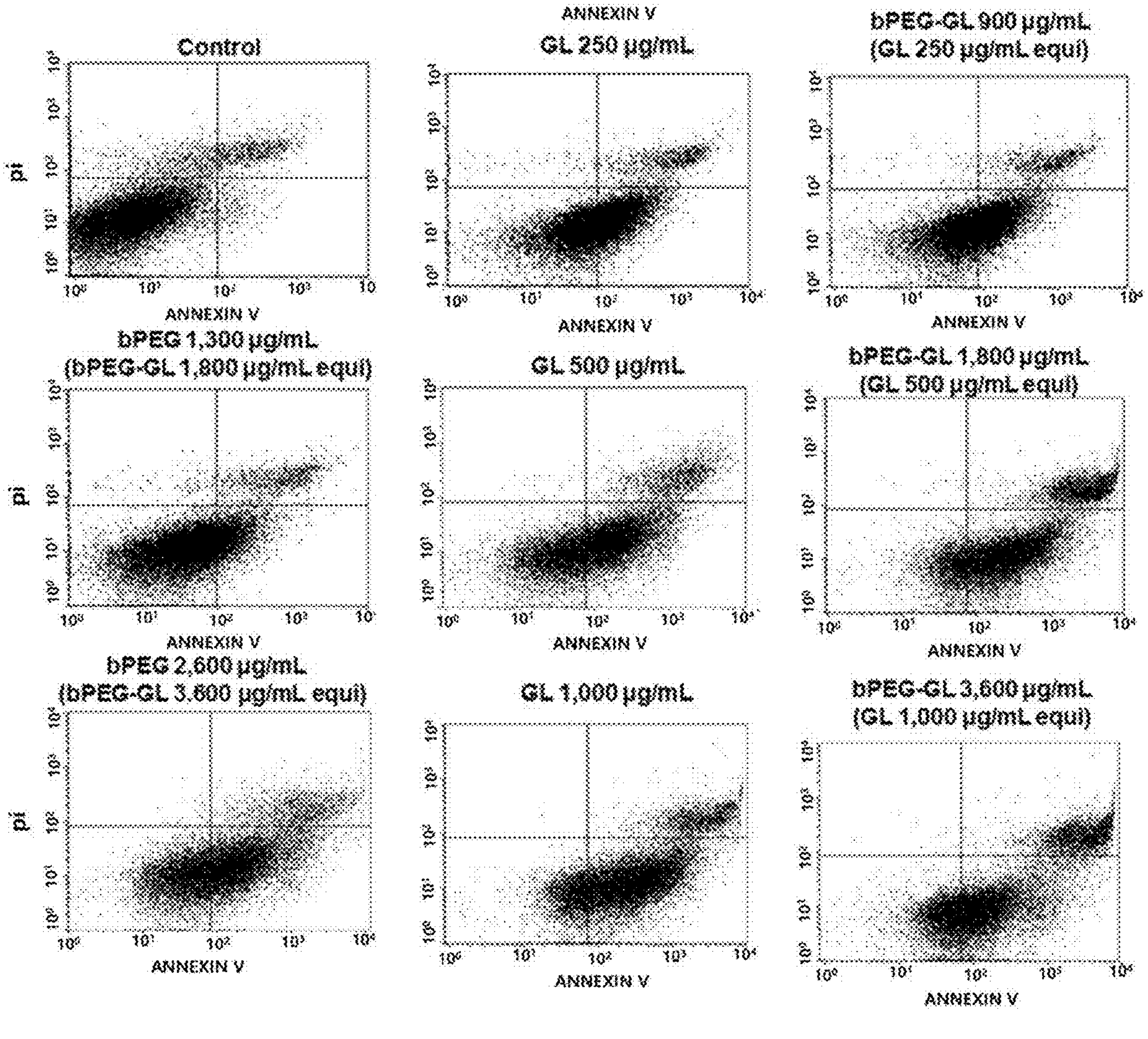
FIG. 12A shows the results of confirming the degree of apoptosis after treating HepG2 cells with glycyrrhizin (GL), branched PEG (bPEG), or a glycyrrhizin-PEG conjugate (bPEG-GL).
Figure 12B:
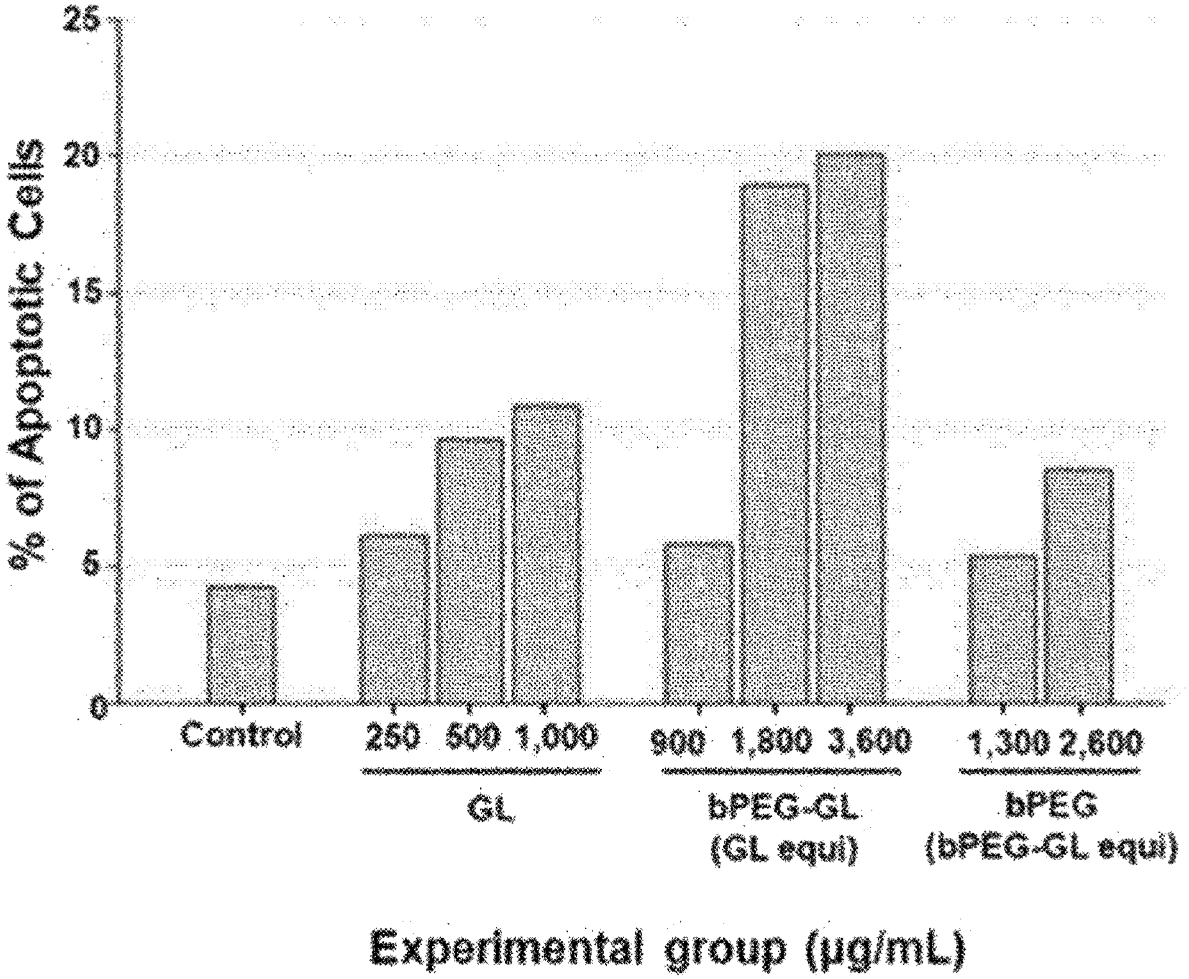
FIG. 12B is a graph showing the results of FIG. 12A.

The analysis results showed that, at the GL equivalent concentration of 500 μg/mL, the proportion of apoptotic cells was 9.63% in the GL-treated group, and 18.92% in the bPEG-GL-treated group, confirming that the apoptosis efficiency of the bPEG-GL-treated group was approximately two times higher. Even at the GL equivalent concentration of 1 mg/mL, the apoptotic cell proportion of the bPEG-GL-treated group was approximately two times higher than that of the GL-treated group (10.86% vs. 20.05%). At 2,600 μg/mL, which is the bPEG-GL equivalent concentration of 3,600 μg/mL, in the bPEG-treated group, the apoptotic cell proportion was 8.54%, indicating no significant effect on apoptosis (FIGS. 12A and 12B).

Example 5: In Vivo Distribution and Pharmacokinetics of Branched PEG-GL 5-1. Confirmation of In Vivo Distribution Each of GL-FITC and bPEG-GL-FITC was dissolved in 1.5 mL of PBS at a concentration of 125 μg/mL based on GL. 100 μL each of the GL-FITC and bPEG-GL-FITC solutions was injected into the tail vein of a C57BL mouse. When a preset time (10 min, 30 min, 3 hr, 6 hr, and 24 hr) passed, the mice were sacrificed, organs were removed, and then fluorescence images were confirmed using FOBI.

Figure 13:
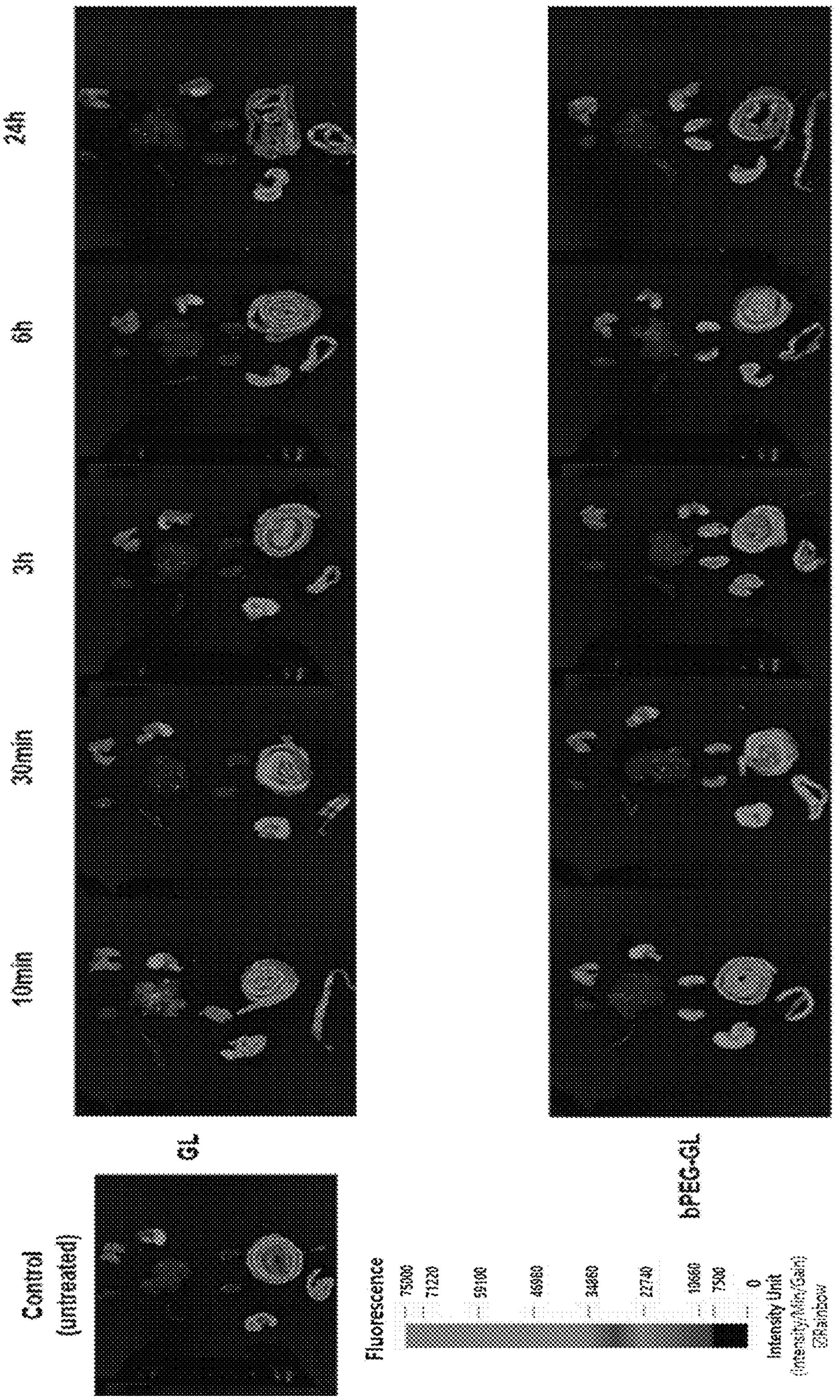
FIG. 13 shows the results of confirming an in vivo fluorescence signal after injecting a mouse with fluorescence-labeled glycyrrhizin (GL) or a fluorescence-labeled glycyrrhizin-PEG conjugate (bPEG-GL).

As a result, fluorescence was visible in the liver and kidney in the GL injection group 10 minutes after injection, but no fluorescence was observed in the corresponding organs at later time points. This implies that GL had been removed. On the other hand, in the bPEG-GL-injected group, the fluorescence of the kidney, which is an organ of the reticuloendothelial system (RES), may be observed at all time points until 24 hours after injection (FIG. 13). It is assumed that the increase in fluorescence time in the bPEG-GL-injected group results from the increase in blood circulation time, compared to the GL-injected group.

5-2. Evaluation of In Vivo Pharmacokinetics 5 mg/kg of GL or 18 mg/kg of bPEG-GL (a GL equivalent amount of the GL-administered group) was injected into the tail vein of a mouse. The mouse was sacrificed at a designated time point after injection and blood was collected through cardiac puncture. The blood collection times were as follows: 1, 3, 5, 10, 30, 60, 120, 150, 360, 720, 1080, and 1440 min (n=4 at each time). The collected blood was centrifuged at 3000 rpm and 4° C. for 20 minutes. Only the plasma, which is the supernatant, was recovered, and 50 μL of the plasma and 100 μL of methyl alcohol (HPLC grade) were mixed and vortexed for 10 minutes. Afterward, the resulting product was centrifuged at 10000 g for 10 minutes.

100 μL of the supernatant was mixed with 900 μL of a mobile phase, and the resulting mixture was filtered using a 0.45 μm syringe filter.

The mobile phase consisted of methanol, acetonitrile, water, and acetic acid in a ratio of 55:23.7:19.2:0.68. The standard curve required for HPLC analysis was prepared as follows: each of 1 mg of GL and 1.8 mg of bPEG-GL was dissolved in 1 mL of the mouse serum. Subsequently, 0, 15.625, 31.25, 62.5, 125, 250, or 500 μg/mL of GL/serum was prepared by continuously diluting 1 mg/mL of the GL/serum solution. HPLC was performed on the blood samples and various concentrations of the GL/serum solutions using a C8 reverse column: flow rate: 1 mL/min; column temperature: 35° C.; UV absorbance: 251 nm; and sample injection amount: 20 μL.

Figure 14:
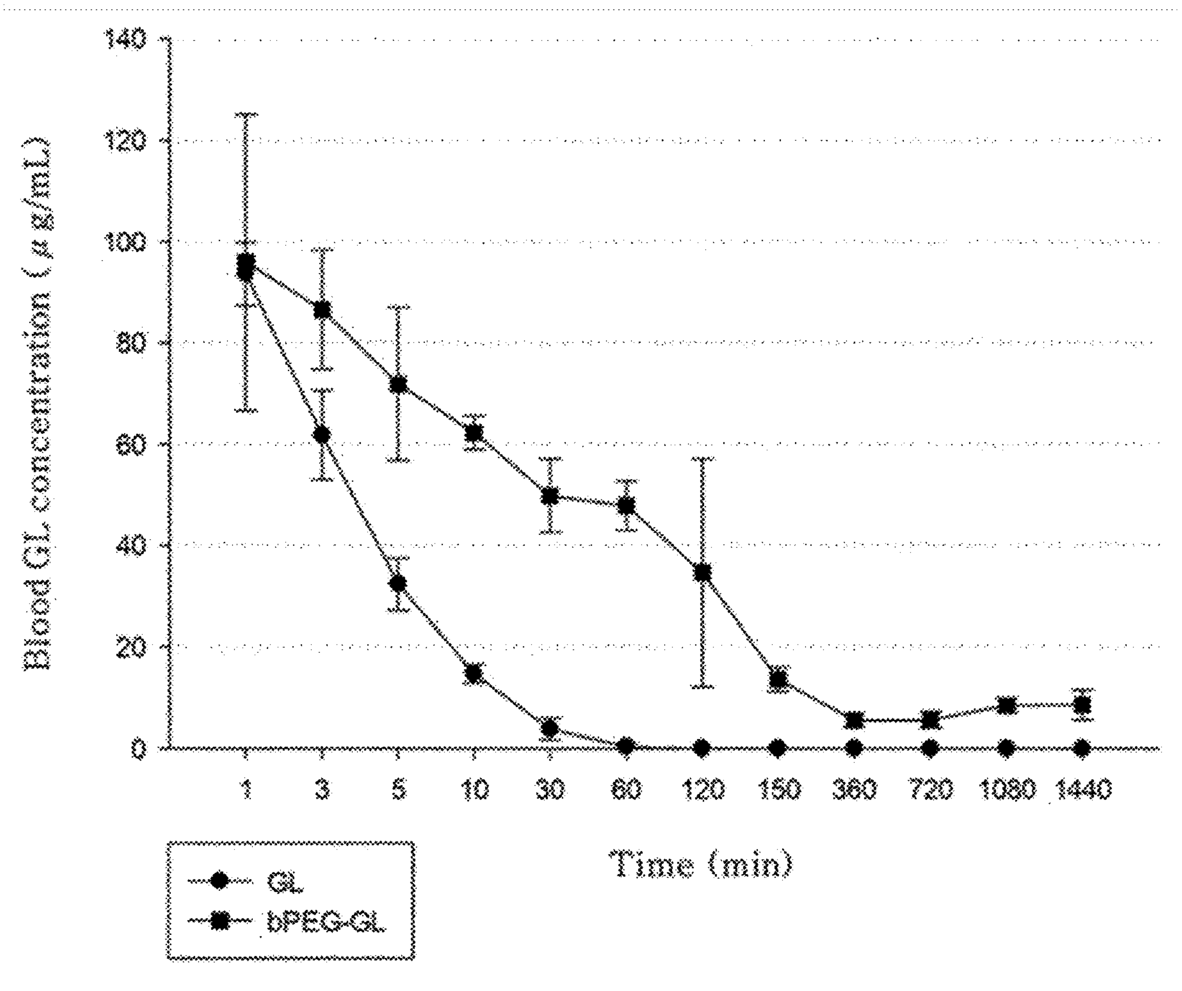
FIG. 14 shows the results of confirming the concentration of glycyrrhizin (GL) or a glycyrrhizin-PEG conjugate (bPEG-GL) present in blood at a given time after injecting a mouse with glycyrrhizin (GL) or glycyrrhizin-PEG conjugate (bPEG-GL).

As a result, the GL-administered group showed a half-life of approximately 4 minutes, but the half-life of bPEG-GL was approximately 1 hour, confirming that the half-life of bPEG-GL was improved approximately 15 times compared to GL (FIG. 14).

Comparative Example: Confirmation of Conjugation of Other Branched PEGs and GL oGL was prepared in the same manner as in Example 1. Various types of branched PEG (4-arm PEG-amine 5 kDa, 4-arm PEG-amine 10 kDa, 8-arm PEG-amine 10 kDa, amine-PEG-amine 2 kDa, amine-PEG-amine 10 kDa, linear PEG 2 kDa, and linear PEG 10 kDa) and oGL were allowed to react in the same manner as in Example 1. However, two reactions for amine-PEG-amine and linear PEG were carried out with PEG and oGL at molar ratios of 1:2 and 1:4, respectively. The resulting products were analyzed by H-NMR and MALDI-ToF.

In Example 2, it was previously confirmed that the C═O peak of the backbone of glycyrrhizin was detected at 5.8 ppm, the proton peak of the carbon next to the primary amine of PEG was detected at 2.8 ppm, and the proton peak of the carbon next to the secondary amine newly produced by the conjugation of bPEG and GL was observed at 3.2 ppm (FIGS. 3A and 3B).

Figure 15A:
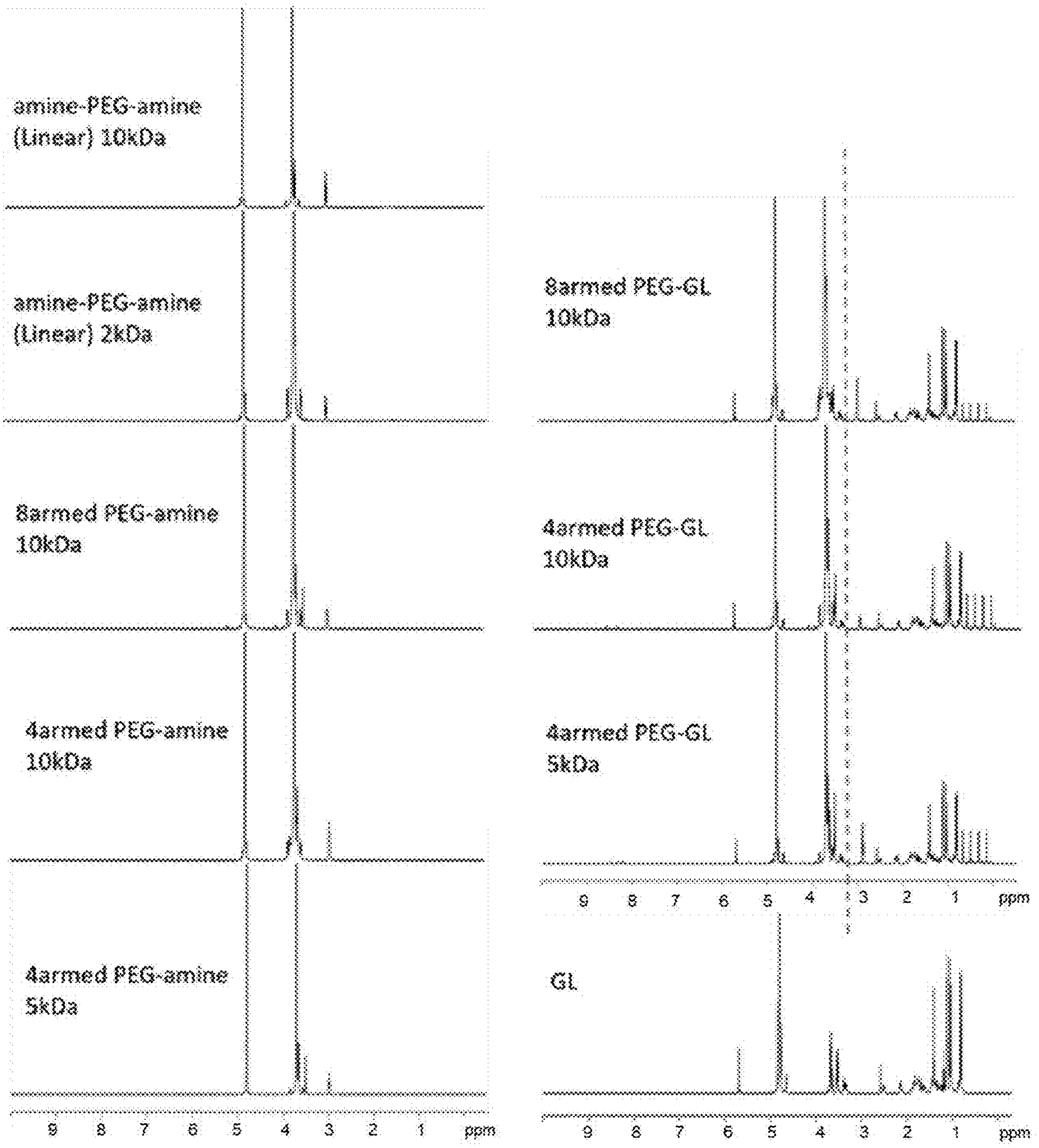
FIGS. 15A and 15B show the H-NMR results of confirming conjugation after reacting glycyrrhizin with various types of branched PEGs.
Figure 15B:
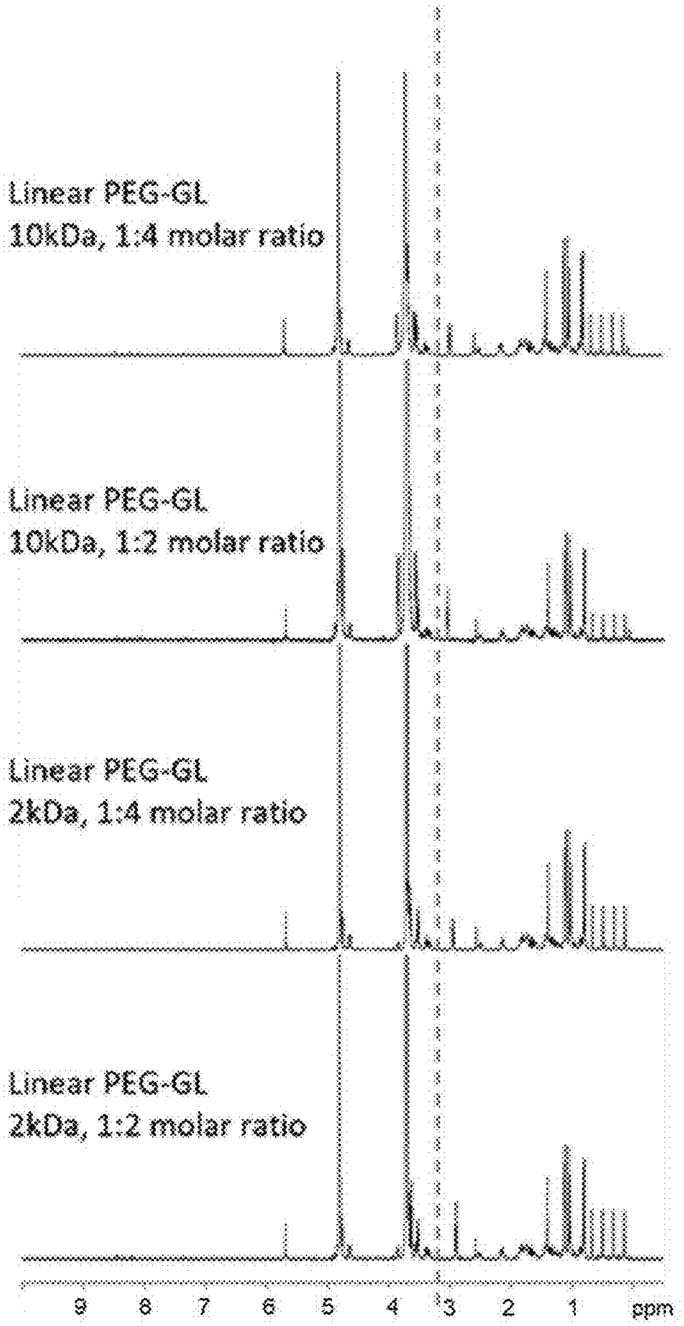
Figure 16A:
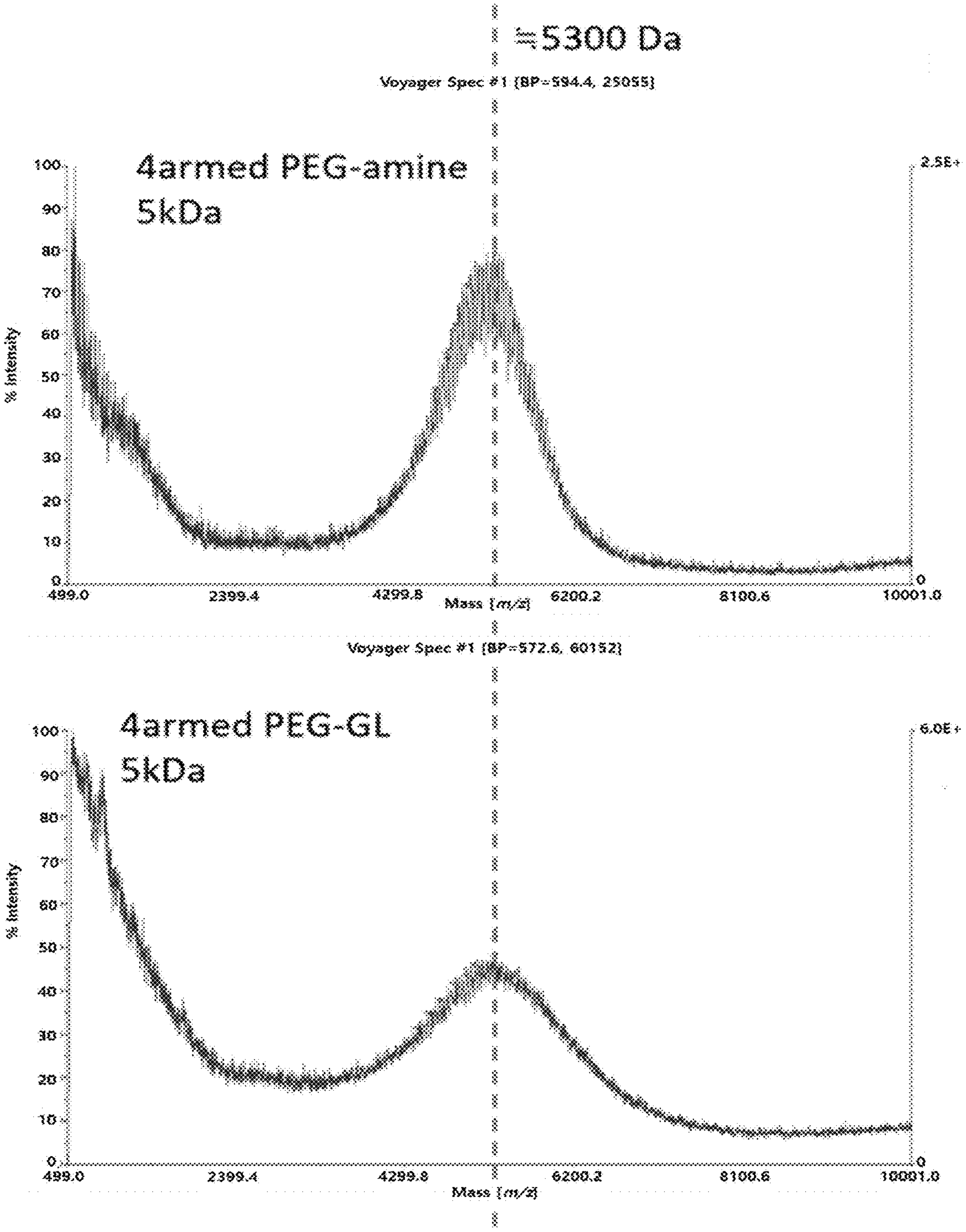
FIGS. 16A to 16C show the results of confirming the molecular weights of materials before and after a reaction through MALDI-TOF after reacting glycyrrhizin with 4-arm PEG-amine 5 kDa, 4-arm PEG-amine 10 kDa, or 8-arm PEG-amine 10 kDa: top-molecular weight of material after reaction; and bottom-molecular weight of PEG before reaction.
Figure 16B:
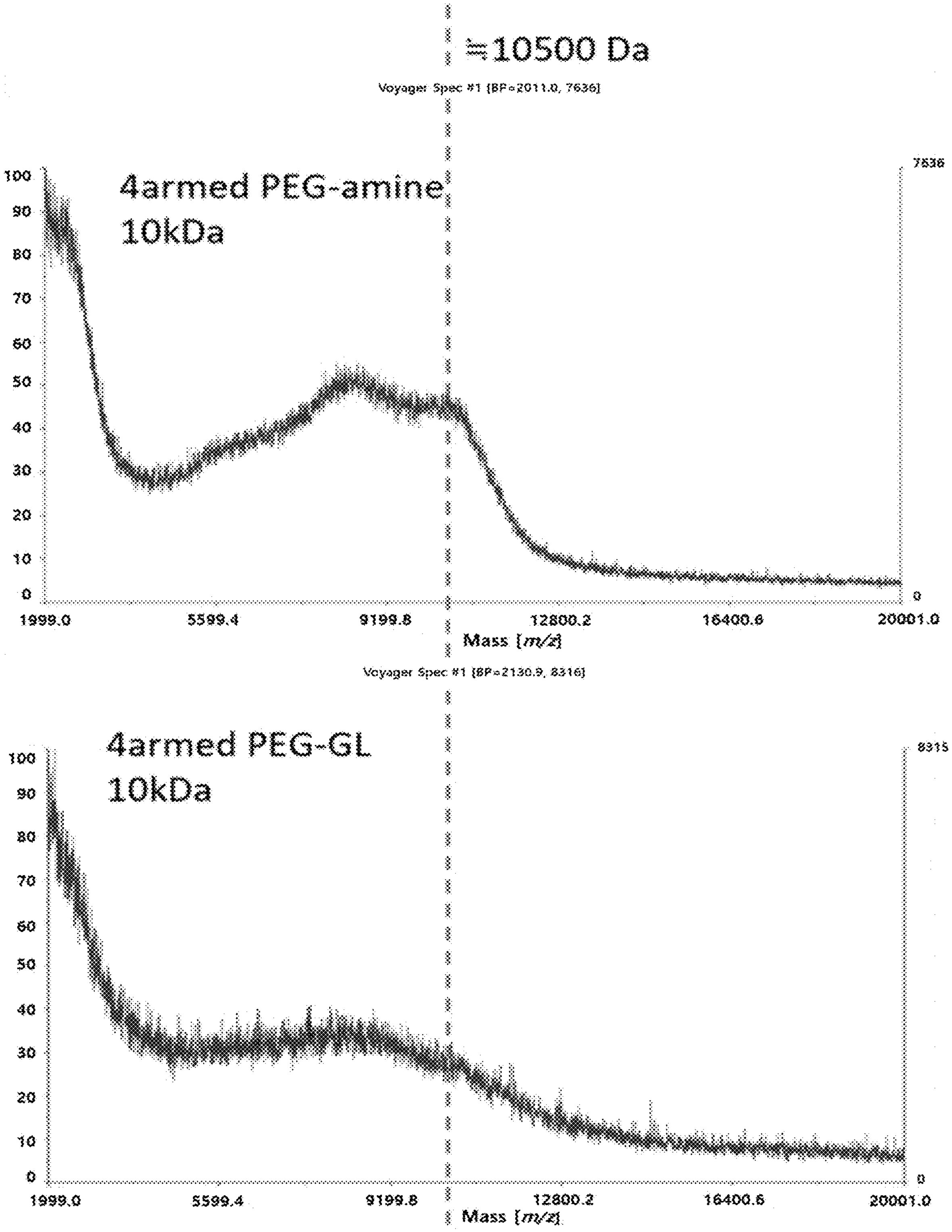
Figure 16C:
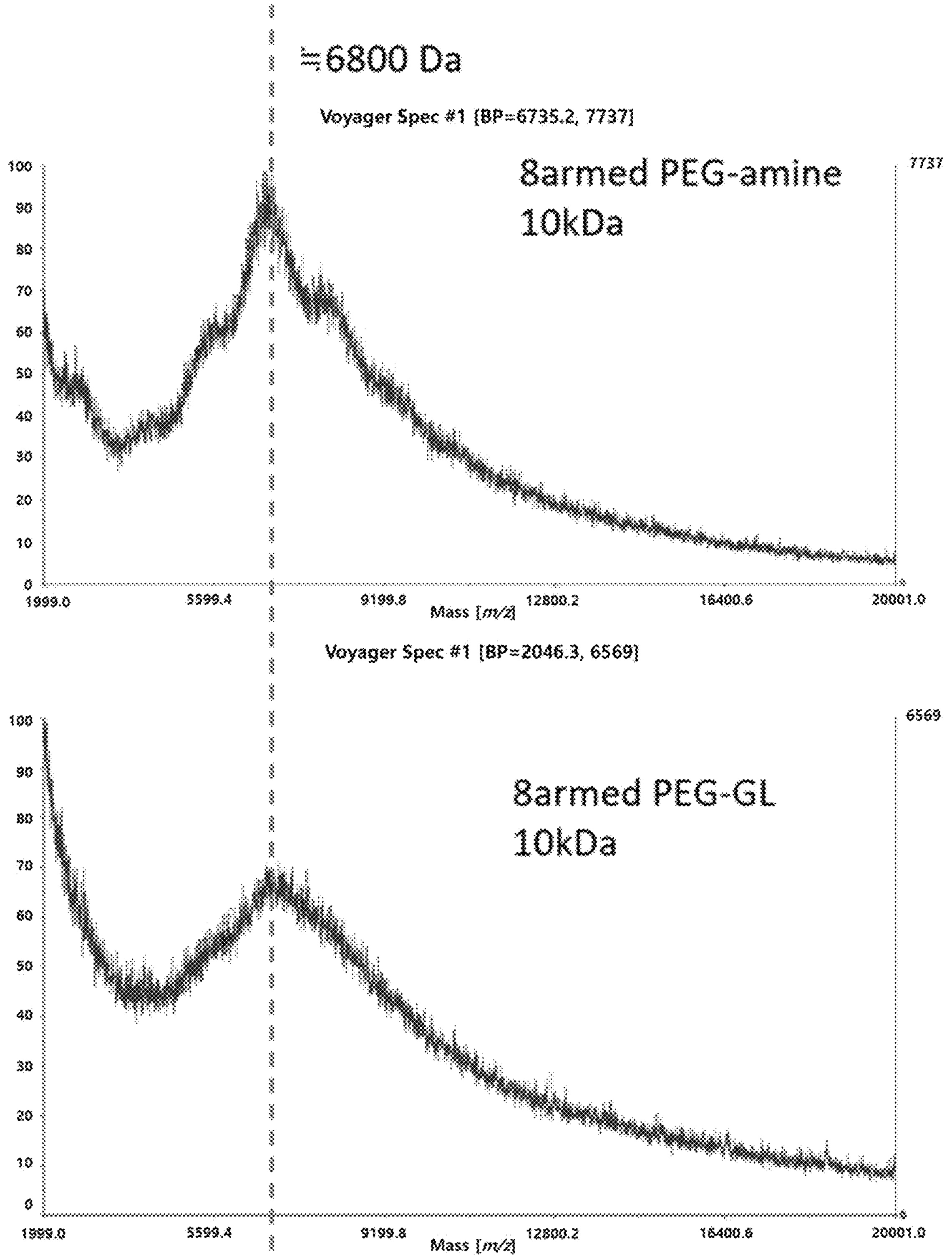
Figure 17A:
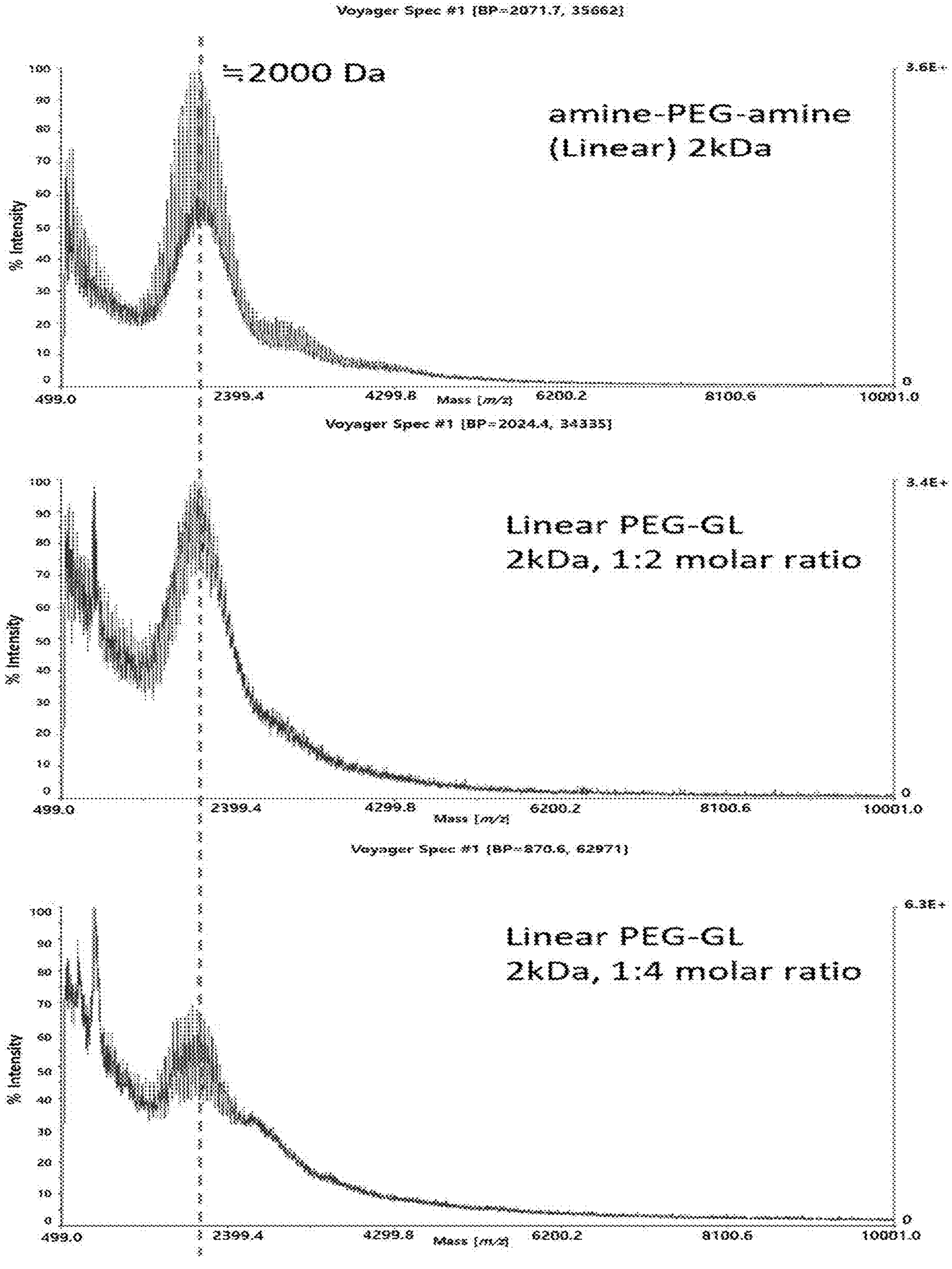
FIGS. 17A and 17B show the results of confirming molecular weights through MALDI-TOF after reacting glycyrrhizin with 2 kDa amine-PEG-amine or 10 kDa amine-PEG-amine at different molar ratios.
Figure 17B:
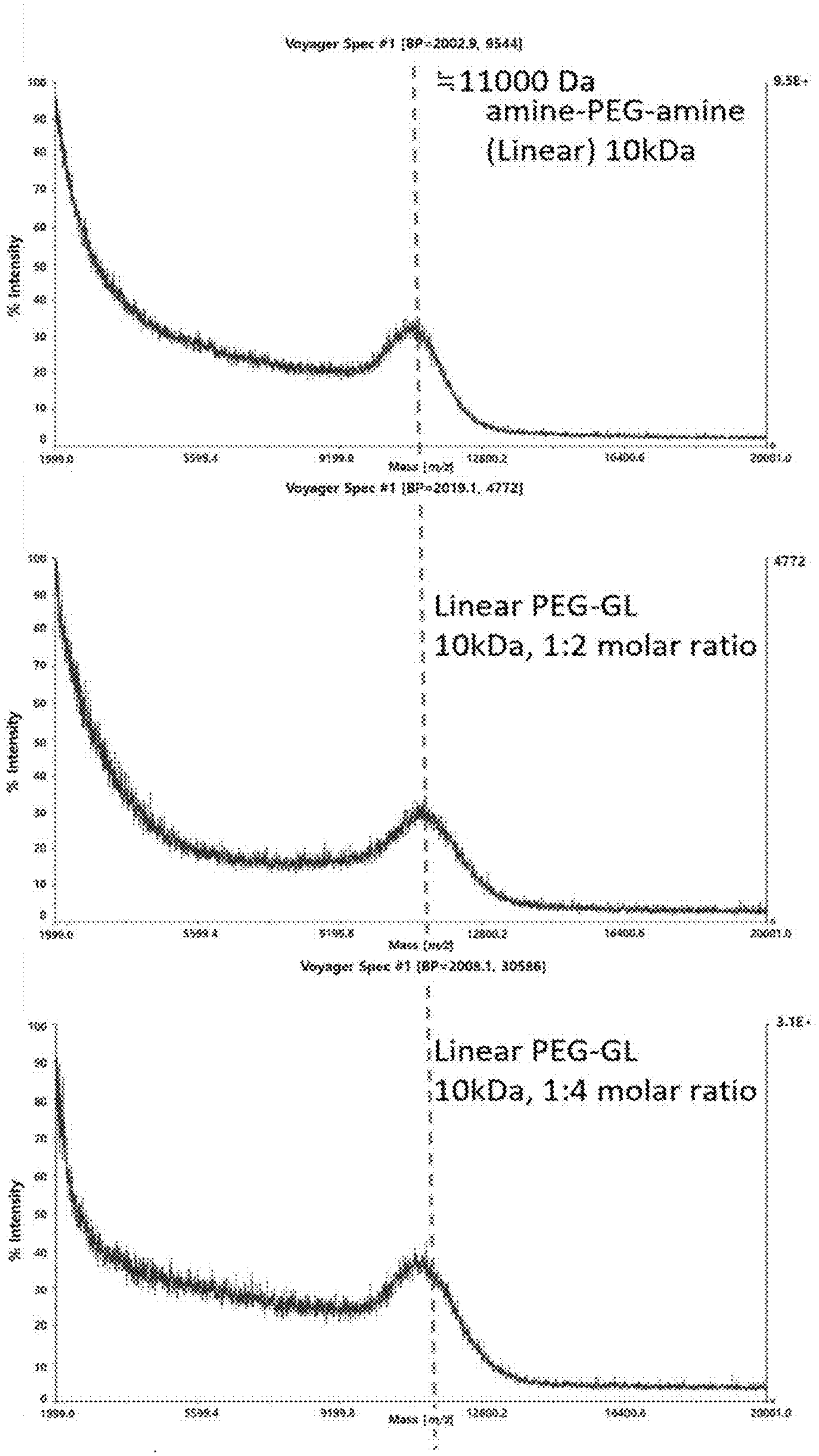

However, when 4-arm PEG-amine 5 kDa, 4-arm PEG-amine 10 kDa, 8-arm PEG-amine 10 kDa, amine-PEG-amine 2 kDa, and amine-PEG-amine 10 kDa were used, the proton peak of the carbon next to the secondary amine could not be confirmed (FIGS. 15A and 15B). This means that bPEG and GL were not conjugated.

The MALDI-TOF analysis results also confirmed that there was no increase in molecular weight or difference in molecular weight between each PEG before the reaction and the material after synthesis (FIGS. 16A-16C and 17A-17B).

The results of this Comparative Example can show that GL binds only to specific PEG (4-arm PEG-amine, 2 kDa).

The invention claimed is:

1. A method of treating cancer comprising administering a pharmaceutical composition for treating cancer comprising the conjugate as an active ingredient as follows:

(a) glycyrrhizin; and (b) branched polyethylene glycol linked to the glycyrrhizin by a covalent bond, wherein the branched polyethylene glycol is 4-arm polyethylene glycol, and its molecular weight is 1 to 4 kDa.

2. The method of claim 1, wherein the glycyrrhizin is in an oxidized form.

3. The method of claim 1, wherein the covalent bond is selected from the group consisting of an amide bond, a carbonyl bond, an ester bond, a thioester bond, and a sulfonamide bond.

4. The method of claim 1, wherein the conjugate has a molar ratio between glycyrrhizin and branched polyethylene glycol ranging from 1:0.5 to 1:5.

5. The method of claim 1, wherein the conjugate is for parenteral administration.

6. The method of claim 1, wherein the branched polyethylene glycol has a molecular weight of 2 kDa.

7. The method of claim 1, wherein the cancer is selected from the group consisting of liver cancer, brain tumor, breast cancer, lung cancer, ovarian cancer, colon cancer, pancreas cancer, cervical cancer, kidney cancer, stomach cancer, prostate cancer, uterine cancer, and bladder cancer.

* * * * *